US012601694B2

(12) United States Patent
Pelc et al.

(10) Patent No.: US 12,601,694 B2
(45) Date of Patent: Apr. 14, 2026

(54) SYSTEM AND METHOD FOR IMPROVED DATA HANDLING IN A COMPUTED TOMOGRAPHY IMAGING SYSTEM

(71) Applicant: GE Precision Healthcare LLC, Waukesha, WI (US)

(72) Inventors: Norbert J. Pelc, Aptos, CA (US); Bruno De Man, Clifton Park, NY (US); Jiahua Fan, New Berlin, WI (US); Lusik Cherkezyan, Libertyville, IL (US); Moa Yveborg Tamm, Yveborg (SE); Jonathan Maltz, Oakland, CA (US)

(73) Assignee: GE Precision Healthcare LLC, Waukesha, WI (US)

( * ) Notice: Subject to any disclaimer, the term of this patent is extended or adjusted under 35 U.S.C. 154(b) by 314 days.

(21) Appl. No.: 18/447,115

(22) Filed: Aug. 9, 2023

(65) Prior Publication Data

US 2025/0052701 A1 Feb. 13, 2025

(51) Int. Cl.
*G01N 23/046* (2018.01)
*A61B 6/03* (2006.01)
(Continued)

(52) U.S. Cl.
CPC ......... *G01N 23/046* (2013.01); *G01N 23/083* (2013.01); *G06T 11/005* (2013.01); *A61B 6/035* (2013.01); *G01N 2223/3303* (2013.01)

(58) Field of Classification Search
CPC ....... A61B 6/032; A61B 6/035; A61B 6/5211; A61B 6/482; A61B 6/4241; A61B 6/5217;
(Continued)

(56) References Cited

U.S. PATENT DOCUMENTS 4,554,633 A 11/1985 Glover
2007/0274456 A1* 11/2007 Holt ..................... G01N 23/046
378/207
(Continued)

FOREIGN PATENT DOCUMENTS

CN 107977043 B 12/2020
WO 2022175259 A1 8/2022

OTHER PUBLICATIONS

EP application 24190966.2 filed Jul. 25, 2024—extended Search Report issued Jan. 15, 2025; 8 pages.

*Primary Examiner* — Irakli Kiknadze

(57) ABSTRACT

Various systems and methods are provided for processing computed tomography (CT) data in a CT imaging system. The CT imaging system comprising an X-ray source configured to emit X-rays, an X-ray detector configured to generate sampled digital detector data and a digital processor configured to process the sampled digital detector data. The method comprises filtering, in the digital processor, the sampled digital detector data to generate filtered detector data and resampling, in the digital processor, the filtered detector data to generate resampled detector data. The resampling comprises a reduction in data size of the filtered detector data. The filtering is performed on at least part of the sampled digital detector data according to a filtering setting and the resampling is performed on at least part of the filtered digital detector data according to a resampling setting, wherein the filtering setting and resampling setting are decoupled.

21 Claims, 19 Drawing Sheets

(51) Int. Cl.
    *G01N 23/083*     (2018.01)
    *G06T 11/00*     (2006.01)

(58) Field of Classification Search
    CPC ... A61B 6/4208; A61B 6/4266; A61B 6/5205;
        A61B 6/4411; A61B 6/00; A61B 6/566;
        A61B 6/563; A61B 6/4283; A61B
        6/4233; A61B 6/56; A61B 6/4464; A61B
        6/4405; A61B 6/4494; A61B 6/42; A61B
        6/4085; G01N 23/083; G01N 23/046;
        G01N 2223/3303; G06T 11/005; G06T
        11/006; G06T 1/20; G06T 5/50; G06T
        5/70; G06T 2211/408; G06T 2211/424;
        G06T 11/003; G06T 11/00; G06T
        2211/436; G06T 2211/421; G06T
        2211/416; G06T 2210/41; G06T 7/0012;
        G06T 2207/30064; G06T 2207/30061;
        G06T 2207/10081; G16H 30/20; G06N
        3/045; G01T 1/24; G01T 1/17; G06V
        40/10; G06V 10/44; G06V 10/56; G06F
        18/24
    USPC .................................................. 378/4, 19, 62
    See application file for complete search history.

(56)            References Cited

U.S. PATENT DOCUMENTS

| | | | |
|---|---|---|---|
| 2012/0170822 A1* | 7/2012 | Litvin ................... | G06T 11/006 |
| | | | 382/131 |
| 2014/0198899 A1* | 7/2014 | Ziskin ................... | G01V 5/226 |
| | | | 378/53 |
| 2017/0244910 A1 | 8/2017 | Karim | |
| 2018/0217277 A1 | 8/2018 | Sjolin | |

* cited by examiner

SYSTEM AND METHOD FOR IMPROVED DATA HANDLING IN A COMPUTED TOMOGRAPHY IMAGING SYSTEM

BACKGROUND

The proposed technology relates to X-ray technology and X-ray imaging, and corresponding data processing tasks and data management. In particular, the proposed technology relates to an X-ray imaging system such as a computed tomography (CT) imaging system and a method of operating such an X-ray imaging system as well as a corresponding computer-program product, for improved data handling.

Radiographic imaging such as computed tomography (CT) imaging systems and other more general X-ray imaging systems have been used for years in medical applications, such as for medical diagnostics and treatment.

Normally, an X-ray imaging system such as a CT imaging system includes an X-ray source and an X-ray detector consisting of multiple detector modules comprising one or many detector elements, for independent measuring of X-ray intensities. The X-ray source emits X-rays, which pass through a subject or object to be imaged and are then received by the detector. The X-ray source and X-ray detector are typically arranged to rotate on a rotating member of a gantry, around the subject or object. The emitted X-rays are attenuated by the subject or object as they pass through, and the resulting transmitted X-rays are measured by the detector. The measured data may then be used to reconstruct images of the subject or object.

It may be useful with a brief overview of an illustrative general X-ray imaging system according to the prior art with reference to FIG. 1A. In this illustrative example the X-ray imaging system 100 comprises an X-ray source 10, an X-ray detector 20 and an associated image processing system 30. In general, the X-ray detector 20 is configured to register radiation from the X-ray source 10, which optionally has been focused by optional X-ray optics or collimators and passed through an object, a subject or a part thereof. The X-ray detector 20 is connectable to the image processing system 30 via suitable read-out electronics, which is at least partly integrated in the X-ray detector 20, to enable image processing and/or image reconstruction by the image processing system 30.

By way of example, a conventional CT imaging system includes an X-ray source and an X-ray detector arranged in such a way that projection images of the subject or object can be acquired in different viewing angles covering at least 180 degrees. This is most commonly achieved by mounting the source and detector on a support, e.g., a rotating member of a gantry, that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

FIG. 1B is a schematic diagram illustrating an example of an X-ray imaging system setup according to the prior art, showing projection lines from an X-ray source through an object to an X-ray detector.

A further development of X-ray imaging is energy-resolved X-ray imaging, also known as spectral X-ray imaging, where the X-ray transmission is measured for several different energy levels. This can be achieved by letting the source switch rapidly between two different emission spectra, by using two or more X-ray sources emitting different X-ray spectra, or by using an energy-discriminating detector which measures the incoming radiation in two or more energy levels. An example of such a detector is a multi-bin photon counting detector, where each registered photon generates a current pulse which is compared to a set of thresholds, thereby counting the number of photons incident in each of a number of energy bins.

A spectral X-ray projection measurement results in a projection image for each energy level. A weighted sum of these projection images can be made to optimize the contrast-to-noise ratio (CNR) for a specified imaging task as described in "SNR and DQE analysis of broad spectrum X-ray imaging", Tapiovaara and Wagner, Phys. Med. Biol. 30, 519.

Another technique enabled by energy-resolved X-ray imaging is basis material decomposition. This technique utilizes the fact that all substances built up from elements with low atomic number, such as human tissue, have linear attenuation coefficients whose energy dependence can be expressed, to a good approximation, as a linear combination of two (or more) basis functions:

$$\mu(E) = a_1 f_1(E) + a_2 f_2(E)$$

where $f_1$ and $f_2$ are basis functions and $a_1$ and $a_2$ are the corresponding basis coefficients. More, generally, $f_i$ are basis functions and $a_i$ are corresponding basis coefficients, where $i=1, \ldots, N$ where N is the total number of basis functions. If there is one or more element in the imaged volume with high atomic number, high enough for a K-absorption edge to be present in the energy range used for the imaging, one basis function must be added for each such element. In the field of medical imaging, such K-edge elements can typically be iodine or gadolinium, substances that are used as contrast agents.

Basis material decomposition has been described in "Energy-selective reconstructions in X-ray computerized tomography", Alvarez, Macovski, Phys Med Biol. 1976; 21(5): 733-744. In basis material decomposition, the integral of each of the basis coefficients, $A_i = \int_\ell a_i dl$ for $i=1, \ldots, N$ where N is the number of basis functions, is inferred from the measured data in each projection ray $\ell$ from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE$$

where $\lambda_i$ is the expected number of counts in energy bin i, E is the energy, $S_i$ is a response function which depends on the spectrum shape incident on the imaged object, the quantum efficiency of the detector and the sensitivity of energy bin i to X-rays with energy E. Even though the term "energy bin" is most commonly used for photon counting detectors, this formula can also describe other energy resolving X-ray imaging systems such as multi-layer detectors, kVp switching sources or multiple source systems.

Then, the maximum likelihood method may be used to estimate $A_i$, under the assumption that the number of counts in each bin is a Poisson distributed random variable. This is accomplished by minimizing the negative log-likelihood function, e.g., see "K-edge imaging in X-ray computed tomography using multi-bin photon counting detectors", Roessl and Proksa, Phys. Med. Biol. 52 (2007), 4679-4696:

$$\hat{A}_1, \ldots, \hat{A}_N = \underset{A_1, \ldots, A_N}{\mathrm{argmin}} \sum_{i=1}^{M_b} \lambda_i(A_1, \ldots, A_N) - m_i \ln \lambda_i(A_1, \ldots, A_N)$$

where $m_i$ is the number of measured counts in energy bin i and $M_b$ is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $a_i$ inside the object (e.g., in CT imaging). In either case, the result of a basis decomposition can be regarded as one or more basis image representations, such as the basis coefficient line integrals or the basis coefficients themselves.

Standard data management procedures for X-ray imaging systems present different approaches to optimize data acquisition, but possibly at a cost of e.g., spatial resolution, noise level and/or system complexity.

Therefore, there is still a general demand for improvements with regard to data management for X-ray imaging systems such as reducing the size of the data, resulting in e.g., faster data communication, reduced storage requirements, and reduced processing time, without having to suffer a reduction in spatial resolution and an increase in noise level.

SUMMARY

This summary introduces concepts that are described in more detail in the detailed description. It should not be used to identify essential features of the claimed subject matter, nor to limit the scope of the claimed subject matter.

It is an object to mitigate, alleviate or eliminate one or more of the above-identified deficiencies in the art and disadvantages singly or in any combination and solve at least the above-mentioned problem.

It is a specific object to provide a method for processing CT data in a CT imaging system.

It is also an object to provide an improved X-ray imaging system.

It is also an object to provide a computer-program to perform the aforementioned method.

These and other objects are met by one or more embodiments of the present invention, as defined by the claims.

According to a first aspect, there is provided a method for processing computed tomography (CT) data in a CT imaging system. The CT imaging system comprises an X-ray source configured to emit X-rays, an X-ray detector configured to generate sampled digital detector data and a digital processor configured to process the sampled digital detector data. The method comprises filtering, in the digital processor, the sampled digital detector data to generate filtered detector data, and resampling, in the digital processor, the filtered detector data to generate resampled detector data. The resampling comprises a reduction in data size of the filtered detector data. The filtering is performed on at least part of the sampled digital detector data according to a filtering setting and the resampling is performed on at least part of the filtered digital detector data according to a resampling setting, and wherein the filtering setting and resampling setting are decoupled.

According to a second aspect there is provided a CT imaging system comprising an X-ray source configured to emit X-rays, an X-ray detector configured to generate sampled digital detector data; and a digital processor configured to process the sampled digital detector data. The digital processor is configured to filter the sampled digital detector data according to a filtering setting to generate filtered detector data and resample the filtered detector data according to a resampling setting to generate resampled detector data. The data size of the resampled detector data is smaller than the data size of the filtered detector data. The filtering setting and the resampling setting are decoupled.

In other words, the proposed technology enables a novel approach of processing and data management for CT imaging systems. Further, the invention caters for a decoupled approach of filtering and resampling the data in a CT imaging system, thereby permitting an increased flexibility in the design of the filter and resampling and choice of image quality, while reducing the size of a data set generated by an X-ray scan, and while improving performance. The improved performance can for example be associated with the reduced size of the data, which may result in faster data communication, reduced storage requirements, and/or reduced processing time, without suffering an intolerable reduction in spatial resolution and/or an intolerable increase in noise level. It should be noted that the proposed technology may be suitable for all three-dimensional (3D) X-ray based medical imaging systems, such as digital mammography imaging systems, interventional imaging systems, fluoroscopic imaging systems, and other radiography imaging systems.

BRIEF DESCRIPTION OF DRAWINGS

The embodiments, together with further objects and advantages thereof, may best be understood by making reference to the following description taken together with the accompanying drawings, in which.

DETAILED DESCRIPTION

Embodiments of the present disclosure will now be described, by way of example, with reference to the figures.

For a better understanding, it may be useful to continue with an introductory description of non-limiting examples of an overall X-ray imaging system in which data processing and transferring according to the inventive concept may be implemented.

Figure 2:
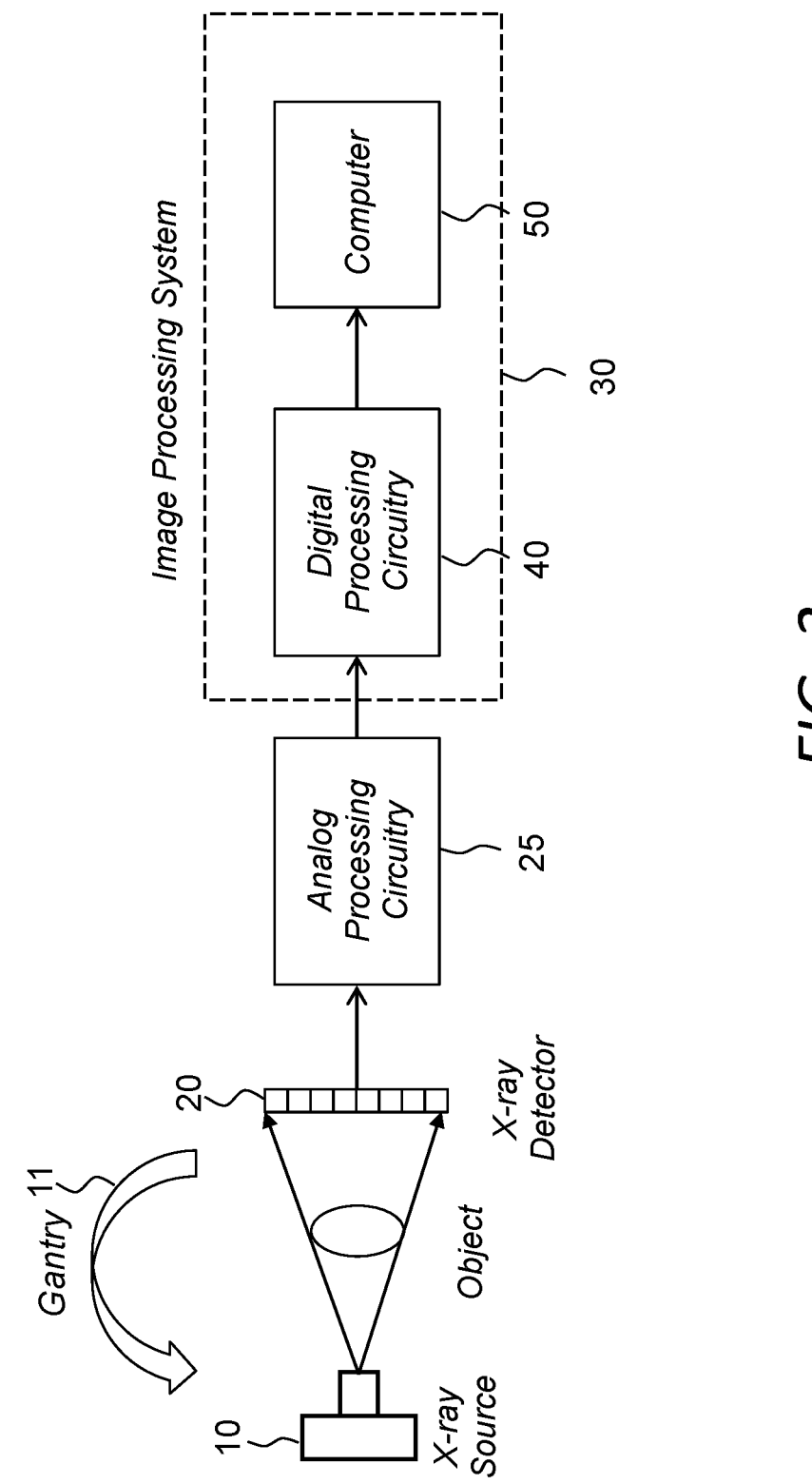
FIG. 2 is a schematic diagram illustrating another example of an X-ray imaging system, such as a CT imaging system.

FIG. 2 is a schematic diagram illustrating an example of an X-ray imaging system 100, such as a CT imaging system, comprising an X-ray source 10, which emits X-rays, an X-ray detector 20 with an X-ray detector, which detects X-rays after they have passed through the object, analog processing circuitry 25, which processes the raw electrical signals from the X-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. The digital processing circuitry 40 may comprise a digital processor. According to an exemplary embodiment, all or part of the analog processing circuitry 25 may be implemented in the X-ray detector 20. The X-ray source and X-ray detector may be coupled to a rotating member of a gantry 11 of the CT imaging system 100.

The overall X-ray detector may be regarded as the X-ray detector system 20, or the X-ray detector 20 combined with the associated analog processing circuitry 25.

In communication with and electrically coupled to the analog processing circuitry 25 is an image processing system 30, which may include digital processing circuitry 40 and/or a computer 50, which may be configured to perform image reconstruction based on the image data from the X-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a CT imaging system, which may include an X-ray source or X-ray tube that produces a fan beam or cone beam of X-rays and an opposing array of X-ray detectors measuring the fraction of X-rays that are transmitted through a patient or object. The X-ray source or X-ray tube and X-ray detector are mounted in a gantry 11 that can rotate around the imaged object.

Figure 3:
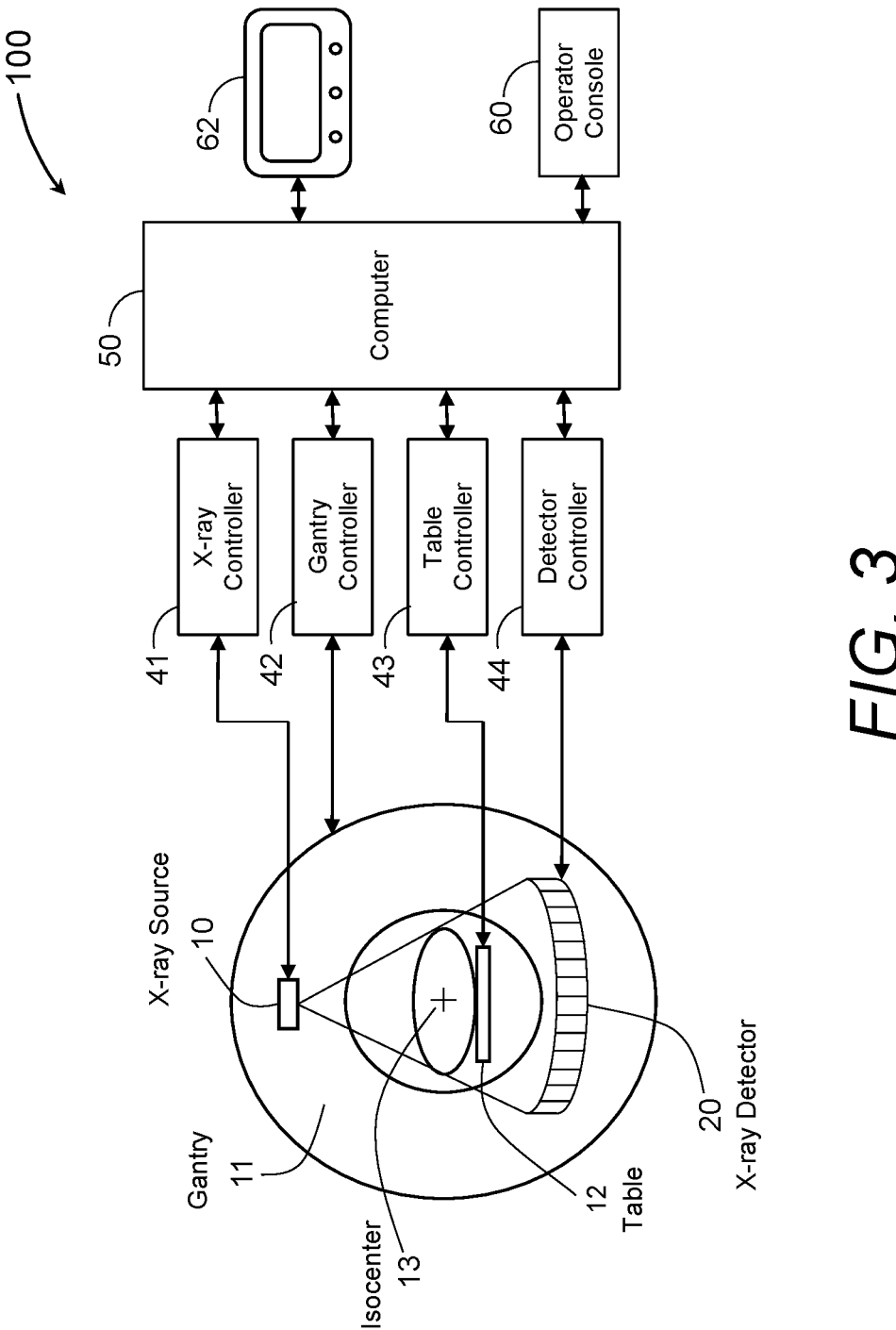
FIG. 3 is a schematic block diagram of a CT imaging system as an illustrative example of an X-ray imaging system.

FIG. 3 schematically shows a CT imaging system 100 as an illustrative example of an X-ray imaging system. The CT imaging system comprises a computer 50 receiving commands and scanning parameters from an operator via an operator console 60 that may have a display 62 and some form of operator interface, e.g., a keyboard, mouse, joy stick, touch screen or other input device. The operator supplied commands and parameters are then used by the computer 50 to provide control signals to an X-ray controller 41, a gantry controller 42 and a table controller 43. To be specific, the X-ray controller 41 provides power and timing signals to the x-ray source 10 to control emission of X-rays onto the object or patient lying on the table 12. The gantry controller 42 controls the rotating speed and position of the gantry 11 comprising the X-ray source 10 and the X-ray detector 20. By way of example, the X-ray detector 20 may be a photon counting X-ray detector. The table controller 43 controls and determines the position of the patient table 12 and the scanning coverage of the patient. There is also a detector controller 44, which is configured for controlling and/or receiving data from the X-ray detector 20.

Figure 1A:
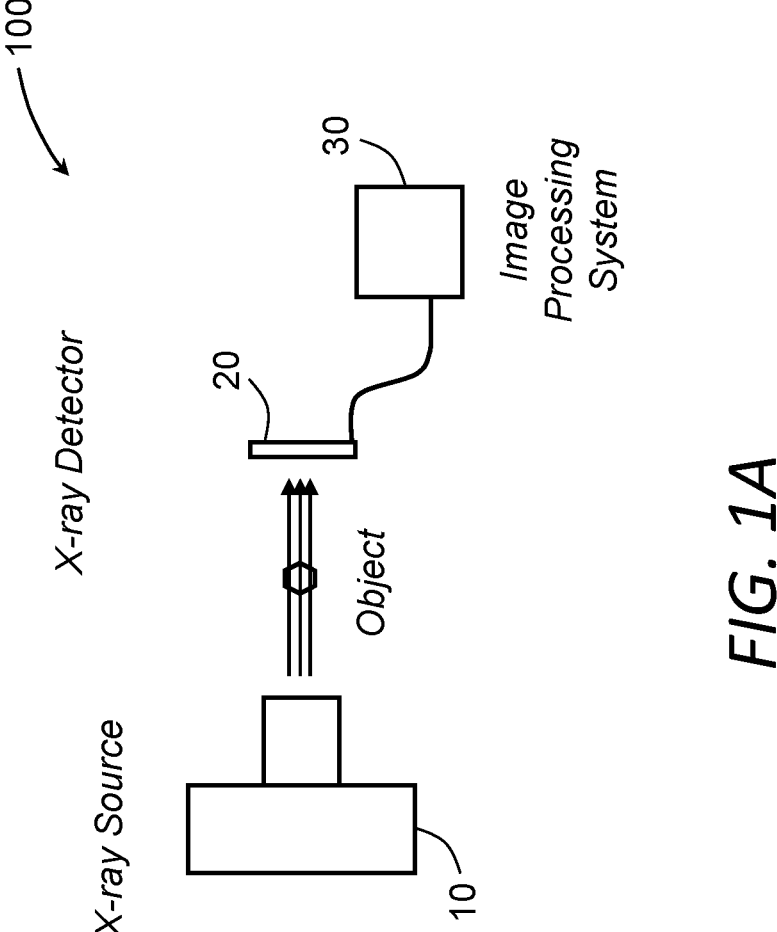
FIGS. 1A and 1B are schematic diagrams illustrating an example X-ray imaging system.
Figure 1B:
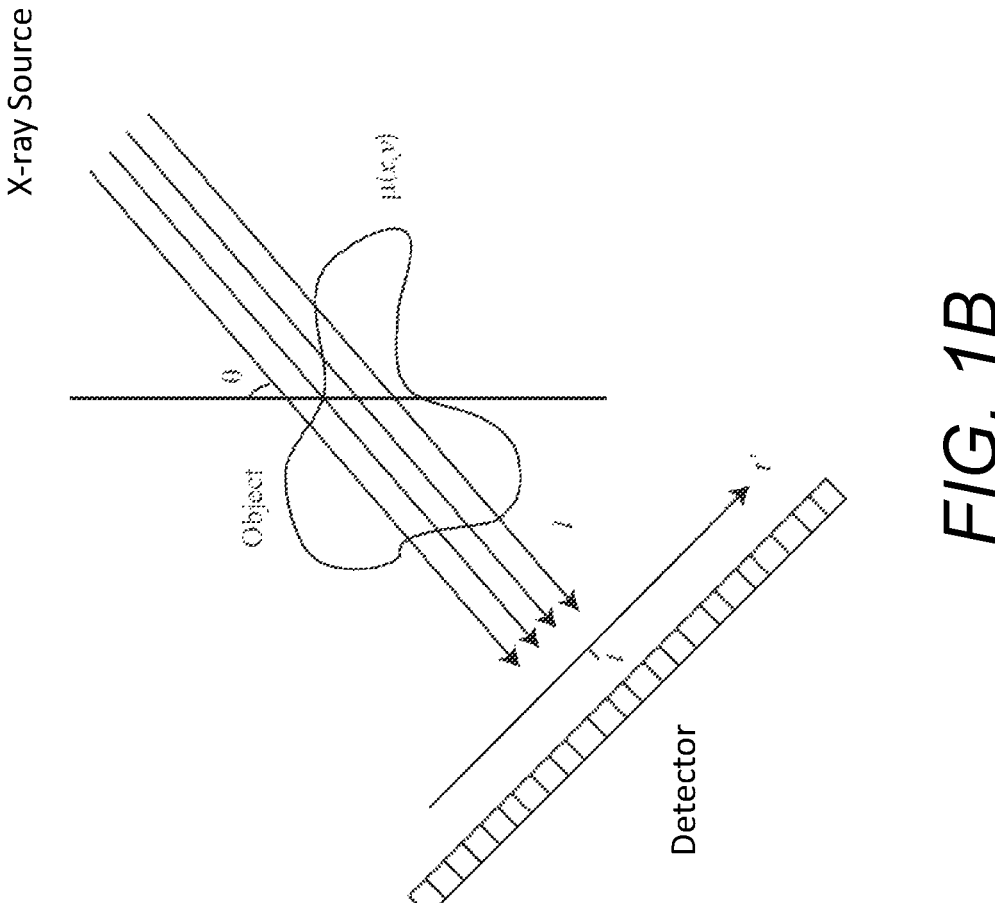

In an embodiment, the computer 50 also performs post-processing and image reconstruction of the image data output from the X-ray detector 20. The computer 50 thereby corresponds to the image processing system 30 as shown in FIGS. 1 and 2. The associated display 62 allows the operator to observe the reconstructed images and other data from the computer 50.

The X-ray source 10 arranged in the gantry 11 emits X-rays. An X-ray detector 20, which may be in the form of a photon counting X-ray detector, detects the X-rays after they have passed through the object or patient. The X-ray detector 20 may for example be formed by plurality of pixels, also referred to as sensors or detector elements, and associated processing circuitry, such as Application Specific Integrated Circuits (ASICs), arranged in detector modules. A portion of the analog processing may be implemented in the pixels, whereas any remaining processing is implemented in, for instance, the ASICs. In an embodiment, the processing circuitry (ASICs) digitizes the analog signals from the pixels. The processing circuitry (ASICs) may also comprise a digital processing, which may carry out further processing operations on the measured data, such as applying corrections, storing it temporarily, and/or filtering. During a scan to acquire X-ray projection data, the gantry and the components mounted thereon rotate about an isocenter 13.

Modern X-ray detectors normally need to convert the incident X-rays into electrons, this typically takes place through the photoelectric effect or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

There are detectors operating in an energy integrating mode in the sense that they provide an integrated signal from a multitude of X-rays. The output signal is proportional to the total energy deposited by the detected X-rays.

X-ray detectors with photon counting and energy resolving capabilities are becoming common for medical X-ray applications. The photon counting detectors have an advantage since in principle the energy for each X-ray can be measured which yields additional information about the composition of the object. This information can be used to increase the image quality and/or to decrease the radiation dose.

Generally, a photon counting X-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter (DAC). The DAC converts a digital setting sent by a controller to an analog voltage to which the heights of the photon pulses can be compared.

A photon counting detector counts the number of photons that have interacted in the detector during a measurement time. A new photon is generally identified by the fact that the height of the electric pulse exceeds the comparator voltage of at least one comparator. When a photon is identified, the event is stored by incrementing a digital counter associated with the channel.

When using several different threshold values, an energy-discriminating photon counting detector is obtained, in which the detected photons can be sorted into energy bins corresponding to the various threshold values. Sometimes, this type of photon counting detector is also referred to as a multi-bin detector. In general, the energy information allows for new kinds of images to be created, where new information is available and image artifacts inherent to conventional technology can be removed. In other words, for an energy-discriminating photon counting detector, the pulse heights are compared to a number N of programmable thresholds (T1-TN) in the comparators and are classified according to pulse-height, which in turn is proportional to energy. In other words, a photon counting detector comprising more than one comparator is here referred to as a multi-bin photon counting detector. In the case of multi-bin photon counting detector, the photon counts are stored in a set of counters, typically one for each energy threshold. For example, one count can be assigned to the highest energy threshold that the photon pulse has exceeded. In another example, counters keep track of the number of times that the photon pulse cross each energy threshold.

As an example, edge-on is a special, non-limiting design for a photon counting detector, where the X-ray sensors such as X-ray detector elements or pixels are oriented edge-on to incoming X-rays.

For example, such photon counting detectors may have pixels in at least two directions, wherein one of the directions of the edge-on photon counting detector has a component in the direction of the X-rays. Such an edge-on photon counting detector is sometimes referred to as a depth-segmented photon counting detector, having two or more depth segments of pixels in the direction of the incoming X-rays. It should be noted that one detector element may correspond to one pixel, and/or a plurality of detector elements corresponds to one pixel and/or the data signal from a plurality of detector elements may be used for one pixel.

Alternatively, the pixels may be arranged as an array (non-depth-segmented) in a direction substantially orthogonal to the direction of the incident X-rays, and each of the pixels may be oriented edge-on to the incident X-rays. In other words, the photon counting detector may be non-depth-segmented, while still arranged edge-on to the incoming X-rays.

By arranging the edge-on photon counting detector edge-on, the absorption efficiency can be increased, in which case the absorption depth can be chosen to any length, and the edge-on photon counting detector can still be fully depleted without going to very high voltages.

A conventional mechanism to detect X-ray photons through a direct semiconductor detector basically works as follows. The energy of the X-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
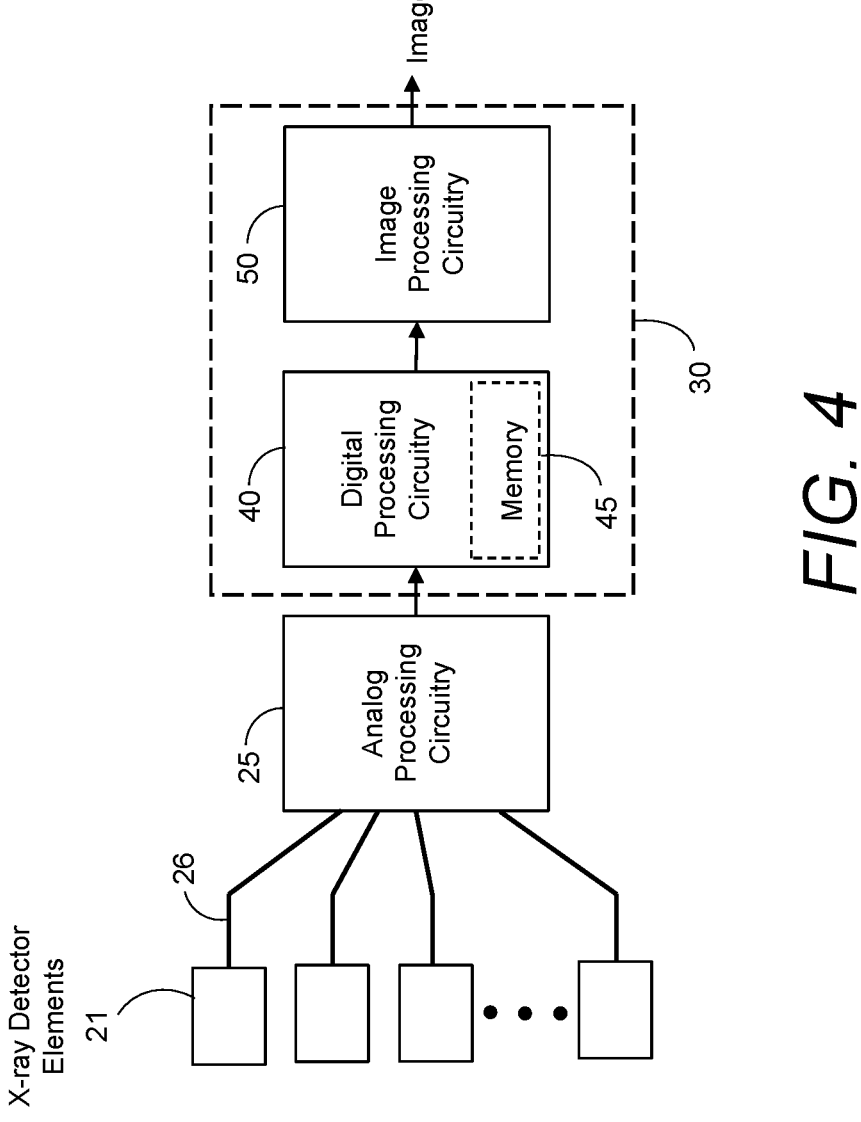
FIG. 4 is a schematic diagram illustrating another example of relevant parts of an X-ray imaging system, such as a CT imaging system.

As illustrated in FIG. 4, signal(s) is/are routed via routing paths 26 from detector elements 22 of the X-ray detector to inputs of analog processing circuitry (e.g., ASICs) 25. It should be understood that the term Application Specific Integrated Circuit (ASIC) is to be interpreted broadly as any general circuit used and configured for a specific application. The ASIC processes the electric charge generated from each X-ray and converts it to digital data, which can be used to obtain measurement data such as a photon count and/or estimated energy. The ASICs are configured for connection to digital processing circuitry so the digital data may be sent to digital processing circuitry 40 and/or one or more memory circuits or components 45 and finally the data will be the input for image processing circuitry 30 or computer 50 in FIG. 2 to generate a reconstructed image.

As the number of electrons and holes from one X-ray event is proportional to the energy of the X-ray photon, the total charge in one induced current pulse is proportional to this energy. After a filtering step in the ASIC, the pulse amplitude is proportional to the total charge in the current pulse, and therefore proportional to the X-ray energy. The pulse amplitude can then be measured by comparing its value with one or more thresholds (THR) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing weather the comparator has been triggered (photon pulse was higher than the threshold) or not.

In a photon counting detector, there is typically a Photon Counting Logic which determines if a new photon has been registered and, registers the photons in counter(s). In the case of a multi-bin photon counting detector, there are typically several counters, for example one for each comparator, and the photon counts are registered in the counters in accordance with an estimate of the photon energy. The logic can be implemented in several different ways. Two of the most common categories of Photon Counting Logic are the non-paralyzable counting modes, and the paralyzable counting modes. Other photon counting logics include, for example, local maxima detection, which counts, and possibly also registers the pulse height of, detected local maxima in the voltage pulse.

There are many benefits of photon counting detectors including, but not limited to: high spatial resolution; less sensitivity to electronic noise; good energy resolution; and material separation capability (spectral imaging ability). However, energy integrating detectors have the advantage of high count-rate tolerance. The count-rate tolerance comes from the fact/recognition that, since the total energy of the photons is measured, adding one additional photon will always increase the output signal (within reasonable limits), regardless of the amount of photons that are currently being registered by the detector. This advantage is one of the main reasons that energy integrating detectors are the standard for medical CT today.

Figure 5:
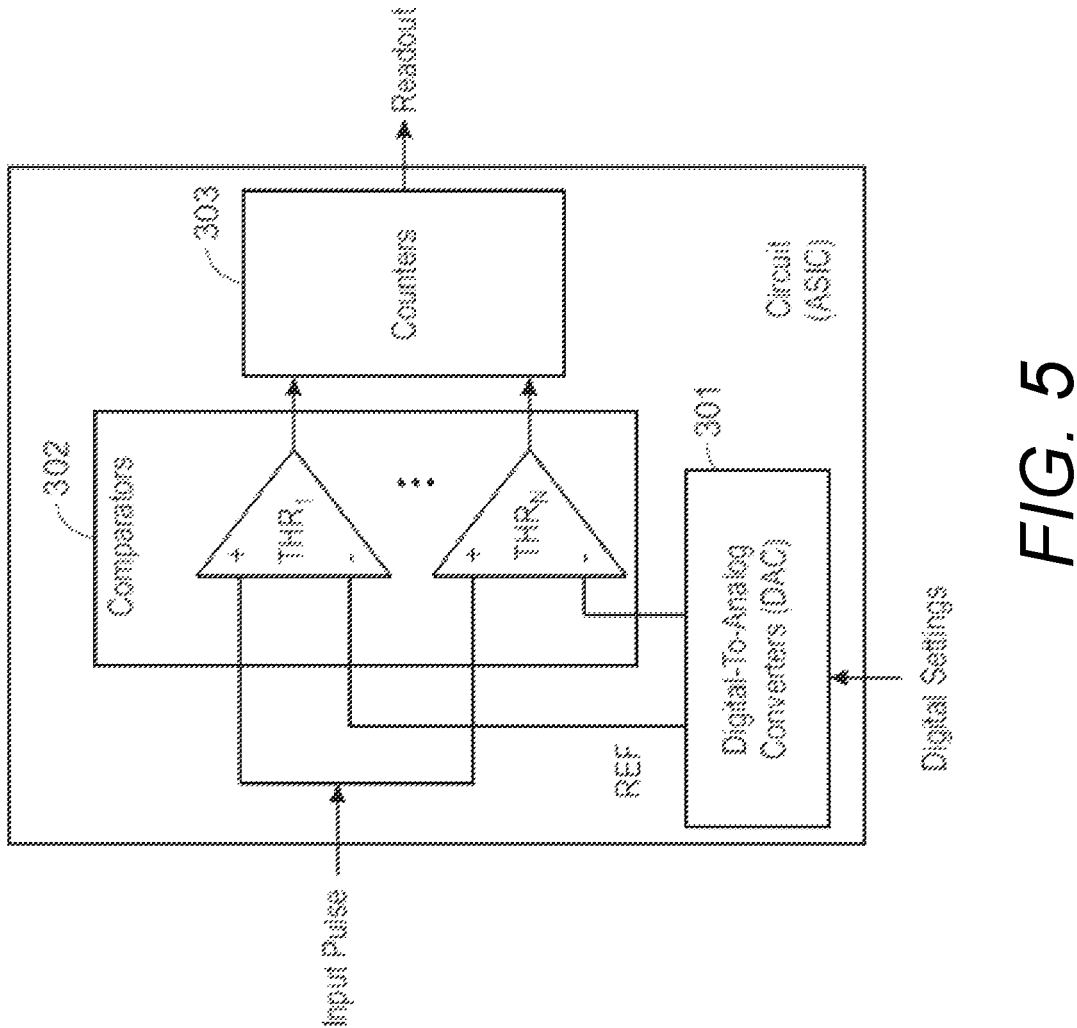
FIG. 5 is a schematic illustration of a photon counting circuit and/or device according to an exemplary embodiment.

FIG. 5 shows a schematic illustration of a photon counting circuit and/or device according to an exemplary embodiment.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g., ASICs. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the voltage pulse to a reference voltage. The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters (DACs), 301 can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

As previously mentioned, when the resulting estimated basis coefficient line integral $\hat{A}_i$ for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients $a_i$ inside the object (e.g., in CT). Anyway, the result of a basis decomposition can be regarded as one or more basis image representations, such as the basis coefficient line integrals or the basis coefficients themselves.

It will be appreciated that the mechanisms and arrangements described herein can be implemented, combined and re-arranged in a variety of ways.

For example, embodiments may be implemented in hardware, or at least partly in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

In the following, non-limiting examples of specific detector module implementations will be discussed. More particularly, these examples refer to edge-on oriented detector modules and depth-segmented detector modules. Other types of detectors and detector modules may also be feasible.

Figure 6:
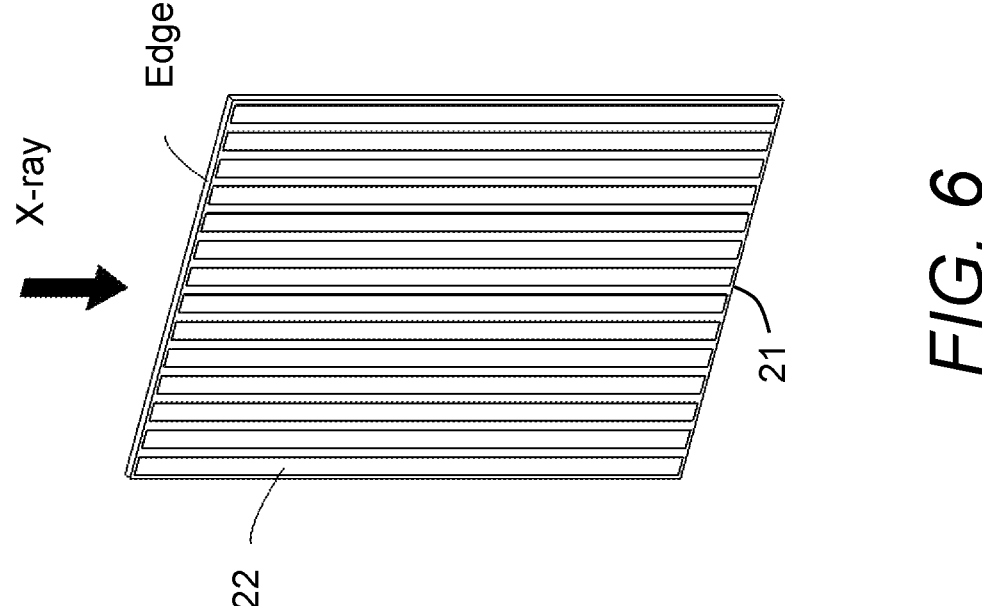
FIG. 6 is a schematic diagram illustrating an example of a semiconductor detector sub-module according to an exemplary embodiment.

FIG. 6 is a schematic diagram illustrating an example of a semiconductor detector sub-module according to an exemplary embodiment. This is an example of a detector module 21 with a semiconductor sensor having a plurality of detector elements or pixels 22, where each detector element (or pixel) is normally based on a diode having a charge collecting electrode as a key component. The X-rays enter through the edge of the detector module.

Figure 7:
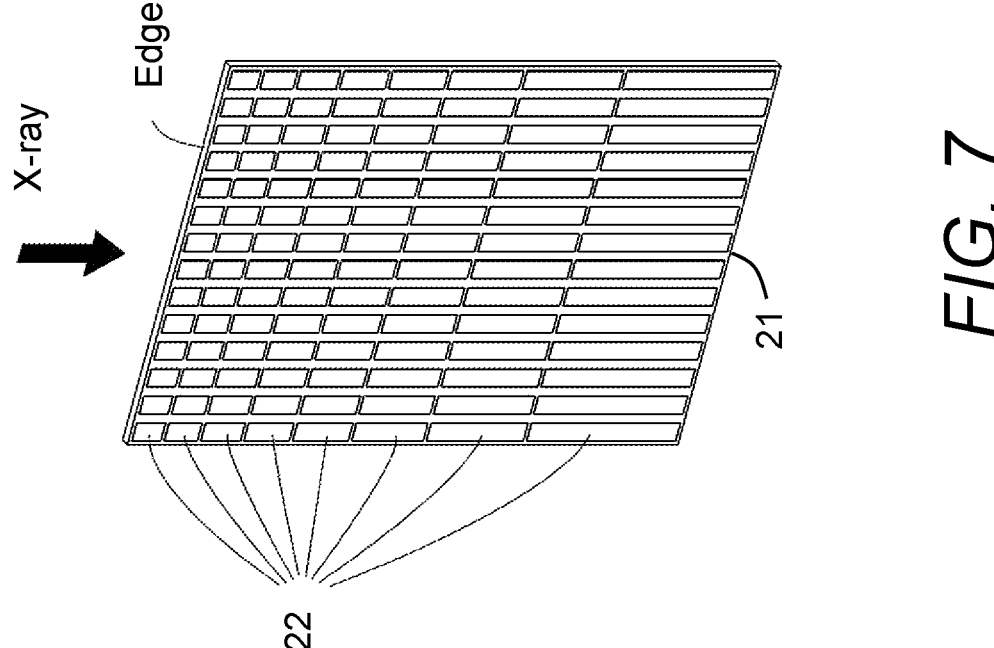
FIG. 7 is a schematic diagram illustrating an example of semiconductor detector sub-module according to another exemplary embodiment.

FIG. 7 is a schematic diagram illustrating an example of semiconductor detector sub-module according to another exemplary embodiment. In this example, the detector module 21 with the semiconductor sensor is also split into a plurality of depth segments or detector elements 22 in the depth direction, again assuming the X-rays enter through the edge of the detector module.

Normally, a detector element is an individual X-ray sensitive sub-element of the detector. In general, the photon interaction takes place in a detector element and the thus generated charge is collected by the corresponding electrode of the detector element.

Each detector element typically measures the incident X-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector, and therefore sometimes also referred to as pixel strips. However, it is also possible to regard a depth-segmented detector as a three-dimensional pixel array, where each pixel corresponds to an individual depth segment/detector element.

The semiconductor sensors may be implemented as so called Multi-Chip Modules (MCMs) in the sense that the semiconductor sensors are used as base substrates for electric routing and for a number of ASICs which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident X-rays if an absorbing cover is placed on top and it can also be protected from scattered X-rays from the side by positioning an absorber also in this direction.

Figure 8B:
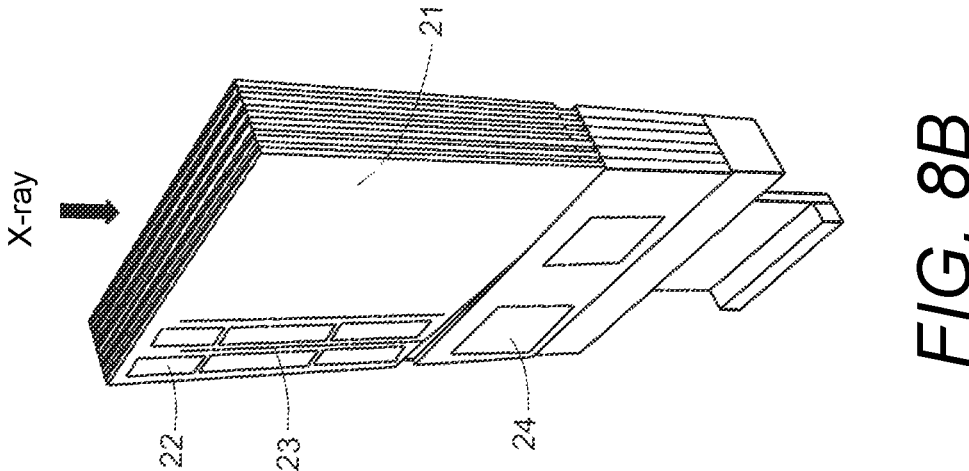
FIG. 8B is a schematic diagram illustrating an example of a set of tiled detector sub-modules, where each detector sub-module is a depth-segmented detector sub-module and Application Specific Integrated Circuits (ASICs) or corresponding circuitry are arranged below the detector sub-modules as seen from the direction of the incoming X-rays.
Figure 8A:
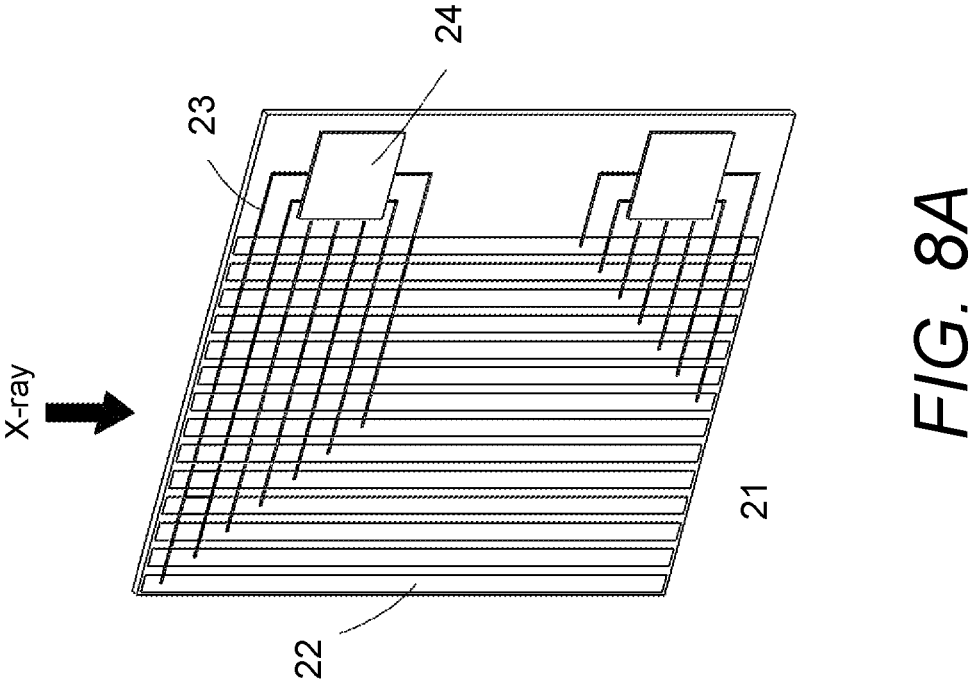
FIG. 8A is a schematic diagram illustrating an example of a semiconductor detector sub-module according to yet another exemplary embodiment.

FIG. 8A is a schematic diagram illustrating a detector module implemented as a MCM similar to embodiments in U.S. Pat. No. 8,183,535. In this example, it is illustrated how the semiconductor sensor 21 also can have the function of a substrate in a MCM. The signals are routed by routing paths 23 from the detector elements 22 to inputs of parallel processing circuits 24 (e.g., ASICs) that are positioned next to the active sensor area. The ASICs process the electric charge generated from each X-ray and converts it to digital data which can be used to detect a photon and/or estimate the energy of the photon. The ASICs may have their own digital processing circuitry and memory for small tasks. And, the ASICs may be configured for connection to digital processing circuitry and/or memory circuits or components located outside of the MCM and finally the data will be used as input for reconstructing an image.

However, the employment of depth segments also brings two noticeable challenges to a silicon-based photon counting detector. First, a large number of ASIC channels has to be employed to process data fed from the associated detector segments. In addition to the increased number of channels due to both the smaller pixel size and the depth segmentation, multi-energy bin further increases the data size. Second, since the given X-ray input counts are divided into smaller pixels, segments and energy bins, each bin has much lower signal and so the detector calibration/correction requires more than several orders of magnitude more calibration data to minimize statistical uncertainty.

Naturally, the several orders of magnitude larger data size slow down both data handling and pre-processing in addition to the need of larger computing resources, hard drive, memory, and central processing unit (CPU) or graphics processing unit (GPU). When the size of data is 10 Gigabytes instead of 10 Megabyte, for example, the data handling time, read and write, can take 1000 times longer.

A problem in any counting X-ray photon detector is the pile-up problem. When the flux rate of X-ray photons is high there may be problems in distinguishing between two subsequent charge pulses. As mentioned above, the pulse length after the filter depends on the shaping time. If this pulse length is larger than the time between two X-ray photon induced charge pulses, the pulses will grow together, and the two photons are not distinguishable and may be counted as one pulse. This is called pile-up. One way to avoid pile-up at high photon flux is thus to use a small shaping time, or to use depth-segmentation.

For pileup calibration vector generation, the pileup calibration data needs to be pre-processed for spit correction. For material decomposition vector generation, the material decomposition data should preferably be pre-processed for both spit and pileup correction. For patient scan data, the data needs to be pre-processed for spit, pileup and material decomposition before the image reconstruction ensues. These are simplified examples to explain "pre-processing" since the actual pre-processing steps can include several other calibration steps as needed, like reference normalization and air calibration. The term "processing" may indicate only the final step in each calibration vector generation or patient scan, but it is used interchangeably in some cases.

FIG. 8B is a schematic diagram illustrating an example of a set of tiled detector sub-modules, where each detector sub-module is a depth-segmented detector sub-module and the ASICs or corresponding circuitry 24 are arranged below the detector elements 22 as seen from the direction of the incoming X-rays, allowing for routing paths 23 from the detector elements 22 to the parallel processing circuits 24 (e.g., ASICs) in the space between detector elements.

Figure 9:
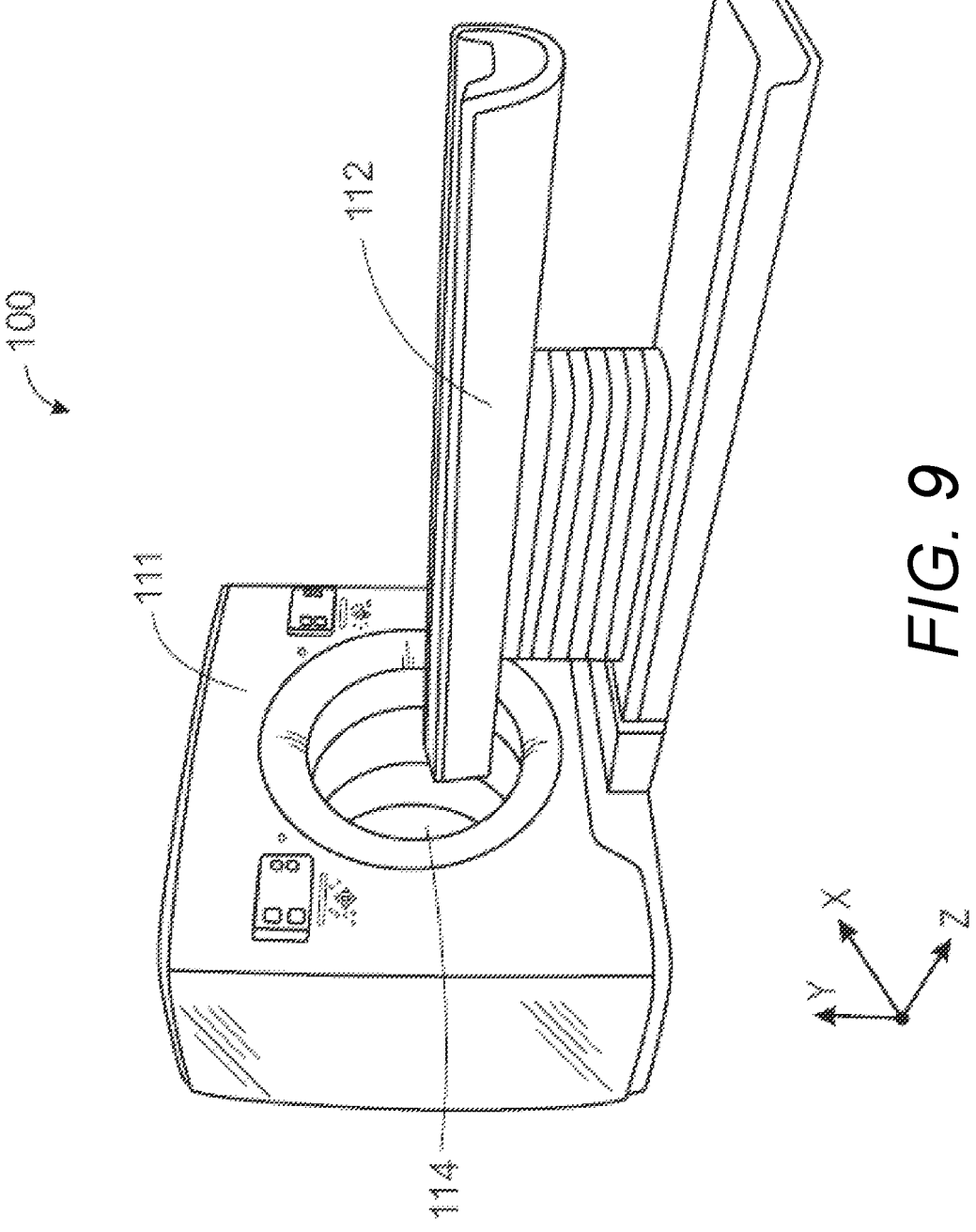
FIG. 9 is a schematic diagram illustrating an example of a CT imaging system.

FIG. 9 is a schematic diagram illustrating an overview example of a CT imaging system. In this schematic example, the overall CT imaging system 100 comprises a gantry 111, a patient table 112 that can be inserted into an opening 114 of the gantry 111 during a patient scan and/or a calibration scan. The direction of the rotational axis of a rotating member of the gantry around a subject or patient being imaged is denoted as the z-direction. The angular direction of the CT imaging system is denoted as the x-direction, and the direction of the incident X-rays is referred to as the y-direction.

It should though be understood that the rotating member and the stationary member of the gantry do not have to be part of a CT system, but may be arranged and/or configured in other ways, e.g., for linear and/or translative relative movement without rotation. As an example, the X-ray source and detector combination may be moved relative to a stationary member of the overall gantry in a linear and/or translative manner. For example, the X-ray source and detector may be moved together as an aggregate assembly unit along the table axis, commonly referred to as the z-axis. Alternatively, the patient table is moved, while the X-ray source and detector combination stands still; the relative movement is the key. This also includes geometric system configurations where the patient may be standing, e.g., in a so-called phone booth type scanner.

Figure 10:
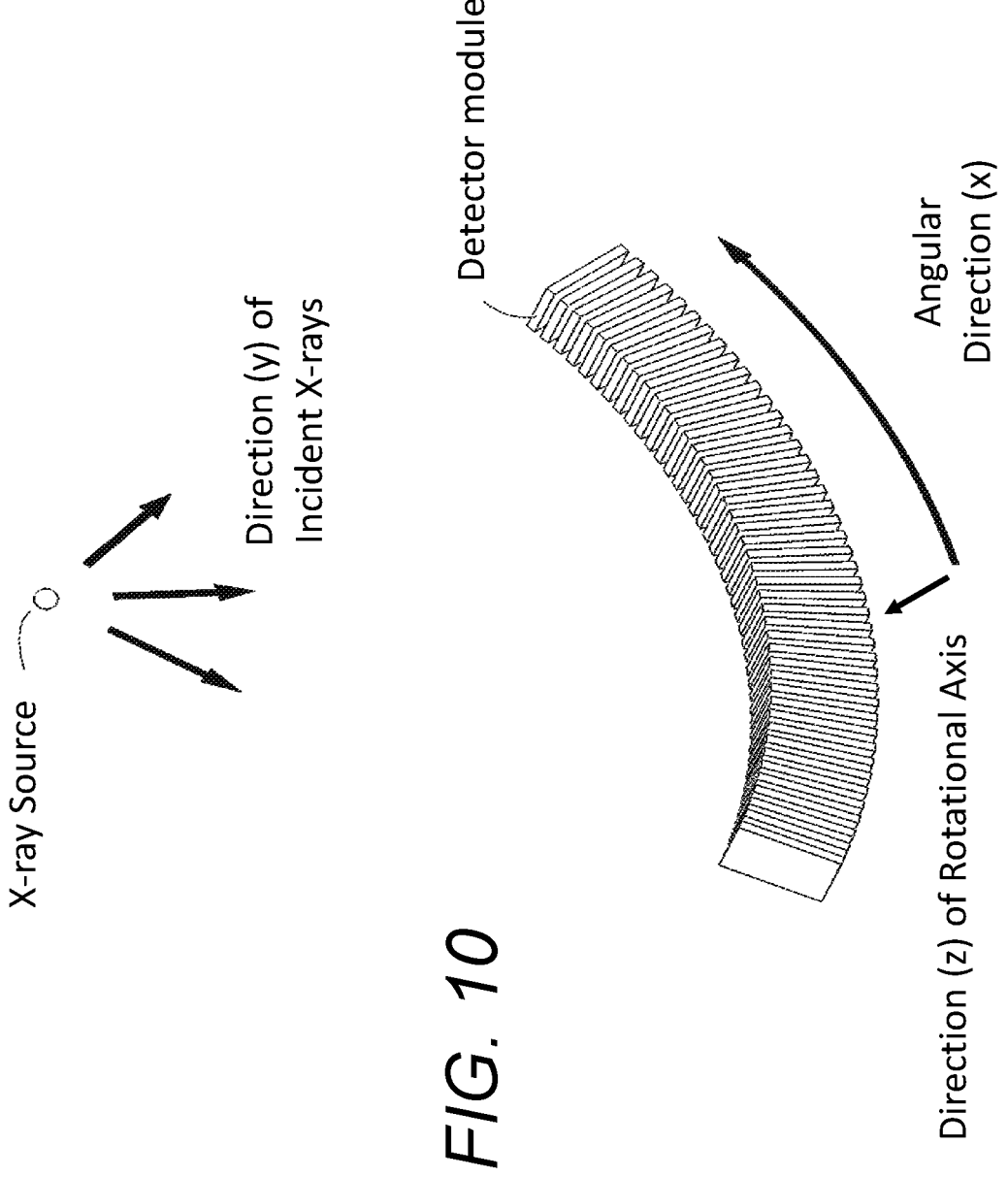
FIG. 10 is a schematic diagram illustrating an example of a design of an X-ray source and X-ray detector system.

FIG. 10 is a schematic diagram illustrating an example of an overall design of an X-ray source-detector system. In this example there is shown a schematic view of an X-ray detector comprising a plurality of detector modules and an X-ray source emitting X-rays. Each detector module may have a set of detector elements defining corresponding pixels. For example, the detector modules may be edge-on detector modules, arranged side-by-side and oriented edge-on pointing back to the X-ray source, and they may be arranged in a slightly curved overall configuration. As mentioned above, the direction of the incident X-rays is referred to as the y-direction. A plurality of detector pixels in the direction of the rotational axis of the gantry (referred as z-direction) enables multi-slice image acquisition. A plurality of detector pixels in the angular direction (referred as x-direction) enables measurement of multiple projections in the same plane simultaneously and this is applied in fan/cone-beam CT. The x-direction is sometimes also referred to as the channel direction. Most detectors have detector pixels in both the slice (z) direction and the angular (x) direction.

Figure 11:
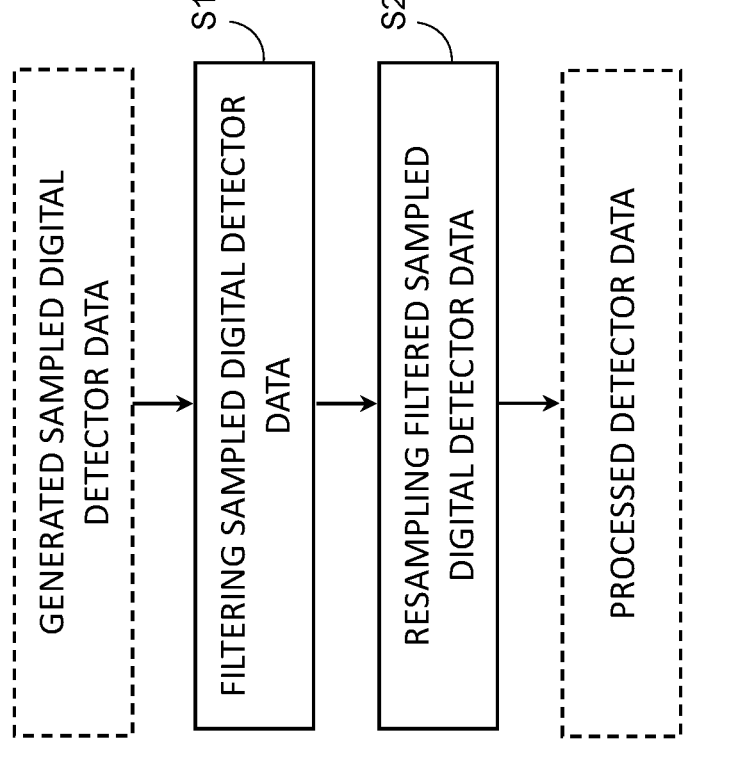
FIG. 11 is a schematic flow diagram illustrating an example of a method for processing data of an X-ray imaging system.

FIG. 11 is a schematic flow diagram illustrating an example of a method for processing data of an X-ray imaging system.

According to a first aspect there is provided a method for processing CT data in a CT imaging system 100. The CT imaging system 100 comprises an X-ray source 110 configured to emit X-rays, an X-ray detector 120 configured to generate sampled digital detector data, and a digital processor 140 configured to process the sampled digital detector data.

The method comprises filtering, in the digital processor, the sampled digital detector data to generate filtered detector data (S1); and resampling, in the digital processor, the filtered detector data to generate resampled detector data, wherein the resampling comprises a reduction in data size of the filtered detector data (S2).

The filtering is performed on at least part of the sampled digital detector data according to a filtering setting and the resampling is performed on at least part of the filtered detector data according to a resampling setting. The filtering setting and the resampling setting are decoupled.

The resampling and filtering settings may be chosen to balance/weigh the filtering and resampling to provide an image of desired quality in a desired manner. The image may have a desired customizable quality, and be produced in a desired customizable time, from an X-ray scan. The X-ray scan may be performed using a certain radiation dose. By "decoupled" it may here be mean that the filtering setting and the resampling setting may be chosen independently of each other and/or the filtering/filtering setting and the resampling/resampling setting are not coupled, or at least not strictly coupled. In other words, the filtering setting and resampling setting may be chosen independently of each other, but e.g., the choice of the resampling setting may be based at least partially on the filtering setting and vice versa. Similarly, decoupled may mean that the resampling setting may be set/chosen to achieve certain effects on the filtered detector data without being constrained by the choice of the filter setting, and still generate an adequate image. The resampling setting and filtering setting may be set/chosen such that they are chosen independently of each other, while the CT imaging system still provides an adequate image with a desired quality.

The filtering setting and resampling setting may be optimized to achieve a certain image quality and/or DQE metric. The filtering and resampling setting may be optimized/based on a radiation dose provided by the CT imaging system during an X-ray CT scan, or a data handling scheme employed by the CT imaging system, such as an operating mode. The image quality may be related to spatial resolution and/or noise and/or aliasing. For example, a filtering setting may be chosen to generate detector data of lesser quality/lower resolution, and the resampling setting may then be chosen to optimize the production of a final image in terms of at least one of image quality, radiation dose, DQW metric and/or data handling. The data handling may be where and when the detector data is processed/filtered/resampled. As another example, the filtering setting and resampling setting may be chosen relative each other in order to achieve a desired reduction of the data size. The data size can be reduced whilst common challenges in data processing such as aliasing and noise can be managed minimized. Therefore, the desired data size reduction can be obtained, without having to be subjected to a reduction in spatial resolution. In some examples of choosing the filtering setting and the resampling setting, some reduction in spatial resolution may be acceptable, in favor to obtain a higher reduction in data size.

It should be noted that the digital processor may comprise digital processing circuitry 40. The digital processing circuitry may carry out processing operations on the sampled digital detector data.

By way of example, the reduction in data size reduces the data size with a reduction factor, and wherein at least one of the filtering setting and resampling setting is associated with the reduction factor. The reduction factor correspond to how much the data is reduced in the resampling step, wherein the filtered detector data is resampled to generate the resampled detector data. The resampled detector data is smaller in data size compared to the filtered detector data.

In another example, the filtering setting and resampled setting are set to achieve a predetermined image quality. The image quality may comprise at least one of spatial resolution, noise aliasing level and signal aliasing. In other words, the filtering setting and the resampled setting are set/chosen/determined/calculated to provide a certain image quality. The image quality may be a set value based on an operating mode and/or a chosen by an operator of the CT imaging system.

By way of example, the filtering may be performed in the spatial and/or the frequency domain. In the spatial domain, the length of the filter may be higher compared to filters used in known methods. A higher length of the filter may involve the filter having a longer length compared to filters used in known methods. For example, the length of the filter may be increased without a loss in spatial resolution and/or in an increase of the noise level, due to the resampling being done in a decoupled manner from the filtering. In the frequency domain, the filter may have a unified amplitude up to a cutoff frequency, to be zero above the frequency. The filter may also have a more gradual transition, such as a Hanning filter and a Hamming filter. Such filters may be referred to as finite impulse response (FIR) filters. The filter may further be designed to achieve a desired passband and/or stopband.

In another example, the resampling may be performed in the spatial and/or the frequency domain. It should be noted that the length of the filter and the amount of resampling may be different/disconnected/decoupled. In particular, if the bandwidth of the filtered signal is reduced by more than the reduction of the resampling frequency, the residual aliasing, if any, may be controlled. This may be desired in CT imaging systems in the case of different approaches of preventing signal aliasing, in particular that of quarter-offset and focal spot wobble. By example, the design of the filtering and resampling may be modeled depending on the relative importance of retaining spatial resolution vs. maximizing detective quantum efficiency (DQE) by avoiding noise aliasing. For a given amount of downsampling, a filter with a higher bandwidth may be used even if some aliasing occurs due to that the CT imaging system maneuver the signal aliasing in other ways. The CT imaging system may then demonstrate higher spatial resolution compared to a system with the same amount of down sampling and a filter with a low enough bandwidth to avoid aliasing. On the other hand, if the efficiency ratio between noise and dose is more important, the filter may be designed to prevent aliasing to a greater extent than simple binning results in. This approach may improve the DQE at low to moderate frequencies, with a possible reduction in spatial resolution compared to binning with the same degree of downsampling.

In yet another example, the resampling comprises a first resampling according to a first resampling setting and a second resampling according to a second resampling setting. The first and second resampling settings may be chosen to improve the image quality. The image quality may have deteriorated after the filtering and/or the first resampling stage. The first resampling and the second resampling may be set/chosen to provide an image of a desired image quality. The first resampling may involve a reduction in data size of the filtered detector data given as input. Furthermore, the first resampling may result in a lowered image quality. The second resampling may be set/chosen to at least partially restore the image quality. In a non-limiting example, the filtering setting and the resampling setting may be associated with a type of operating mode. The operating mode may correspond with reduced data sizes, which may further offer faster data communication, reduced storage requirements, and/or reduced processing time. Accordingly, the CT imaging system may be configured to run in one or more operating modes, wherein each operating mode may balance/weight the filtering and resampling to provide an image of desired quality in a desired way. The image may have a desired quality, and be produced in a desired time, based on an X-ray scan with a desired radiation dose. The operating mode may e.g., optimize the filtering and resampling setting to achieve a certain image quality, radiation dose, DQE metric and/or data handling scheme.

In an exemplifying practical example, the operating mode may be associated with an image quality, a DQE metric and/or a data handling scheme.

The data handling scheme may comprise operational settings/instructions of where in the CT system the data is processed, and in what way. Thus, the data handling scheme is related to how fast an operator may receive a final image for diagnosis. The data handling scheme relates to how much data is processed, where in the CT imaging system and when, also it relates to how and when data is transferred. For example, a CT system may perform filtering and resampling on the rotating side of the gantry of the CT system and then transfer the resampled data to the stationary side where the remaining processing for generating a final image is performed. This may improve the speed at which an adequate image may be generated to be viewed by an operator or technologist of the CT imaging system.

It should be understood that the CT imaging system may comprise any 3-D X-ray based medical imaging modalities. For example, the CT imaging system may comprise a general tomography system which is adapted to taking images from different angles and combining the information in them to create an image volume where every slice can be individually reviewed. The CT imaging system may comprise a CT system adapted to use an angular range of a full 180-degree range and/or a limited angular range. In other words, the CT system may comprise a normal computed tomography system using a full 180-degree range, or a breast tomosynthesis system, also called mammogram, using a limited angular range. In an example, the CT imaging system may be configured to be run in an operating mode, wherein the operating mode balances at least two parameters depending on the configuration of the operating mode. The parameters that are being balanced may be radiation dose, DQE and parameters related to data handling schemes. For example, a first operating mode may be optimized/configured for a quick image generation, i.e., to provide a faster process to a final image. The first operating mode may thus balance parameters to provide an image faster, e.g., by reducing the size of the data in the resampling and lowering the resolution, but still achieving adequate image quality by performing the filtering and resampling in a decoupled manner to adjust for the reduced image quality due to the data reduction. A second operating mode may be optimized/configured for a reduced radiation dose while still providing a resampled data set with adequate image quality and/or DQE metric, while also being reduced in data size, by adjusting the filtering and resampling in a decoupled manner.

In an embodiment, the CT imaging system 100 may comprise a gantry 111 including a rotating member on a rotating side 102 and a stationary member on a stationary side 104. The rotating member and the stationary member may be communicatively coupled via a data communication system 160, wherein the rotating member may comprise the X-ray source 110, the X-ray detector 120 and the digital processor 140.

Figure 17:
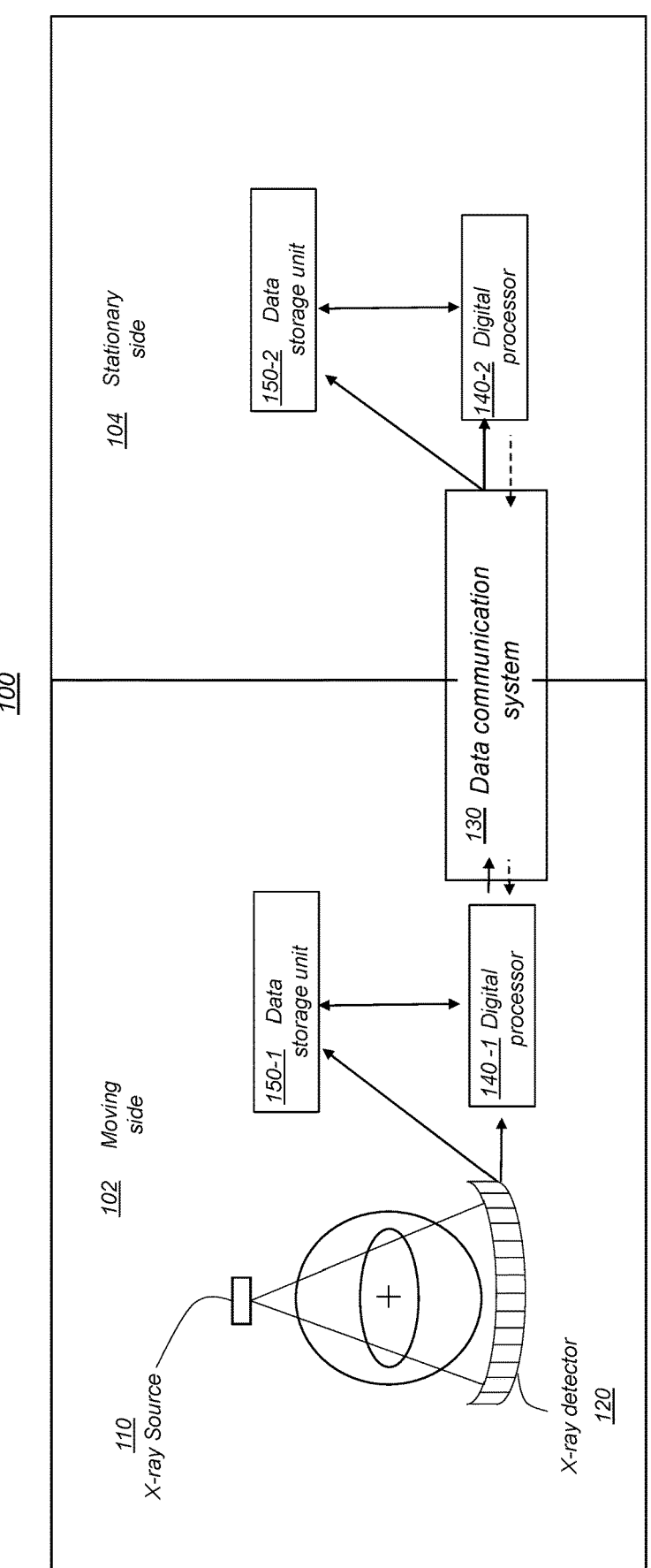
FIG. 17 is a schematic diagram illustrating an example of a CT imaging system according to an exemplary embodiment.

In a particular example, illustrated in FIG. 17, the digital processor 140 may comprise a first digital processor 140-1 arranged on the rotating member and a second digital processor 140-2 arranged on the stationary member. The first and/or second digital processor may be configured to perform at least part of the filtering and/or the resampling. In a non-limiting example, the first digital processor may be configured to filter at least part of the detector data to generate filtered detector data, and resample the filtered detector data to generate resampled detector data, wherein the resampled detector data is transferred to the stationary side, where a final image may be created based on the resampled detector data. The resampled detector data may be smaller in size compared to the filtered detector data. This may result in faster data communication, reduced storage requirements, reduced processing time and faster image generation. In a further example, the filtering may be performed by the first digital processor and the resampling by the second digital processor. This is advantageous in that a part of the processing may be executed before transferring the data between the rotational and stationary side. This may result in e.g., faster image acquisition, and thus enables a diagnosis to be established faster. Furthermore, it may allow more efficient usage of the components of the CT imaging system.

Figure 12:
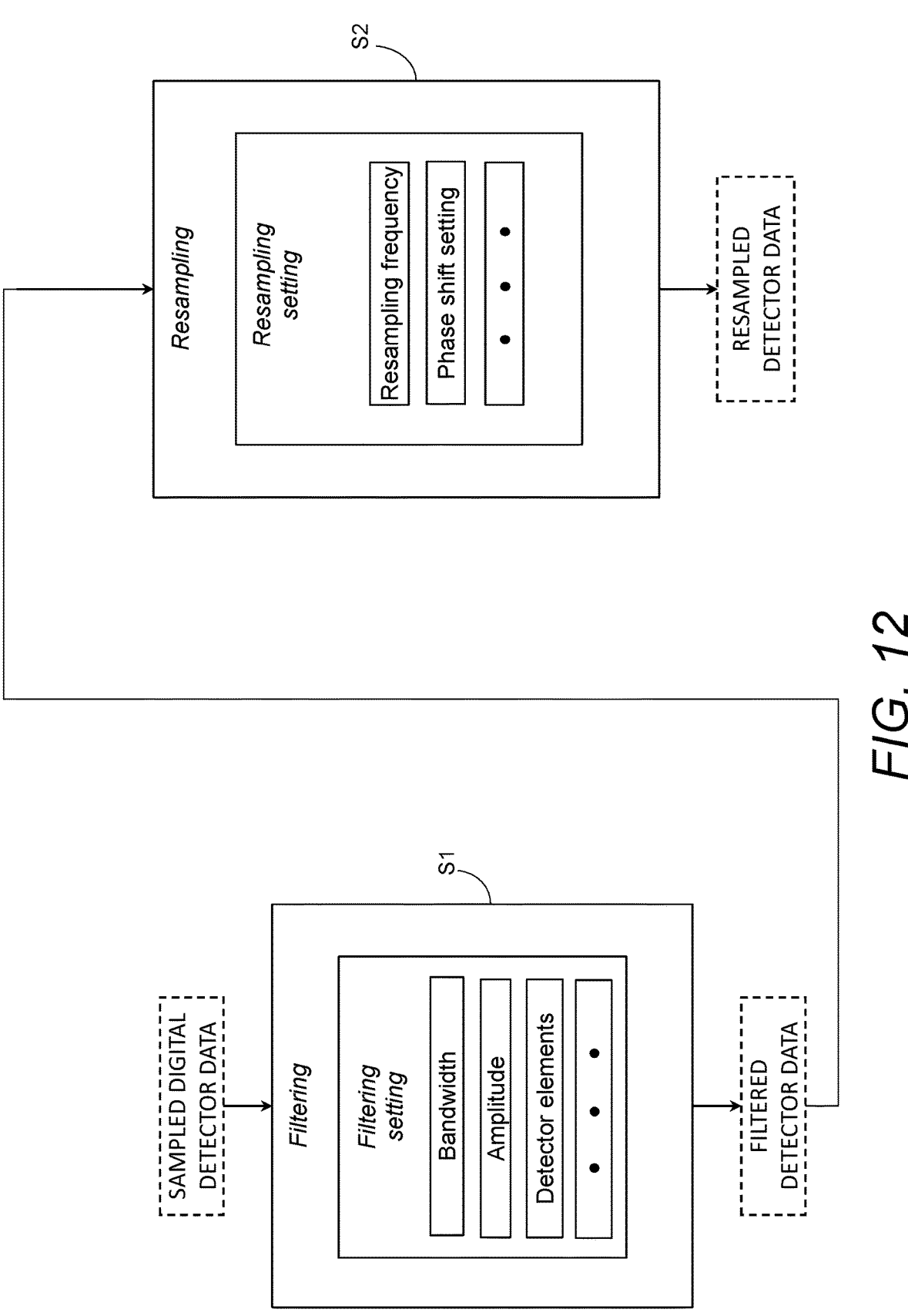
FIG. 12 is a schematic flow diagram illustrating an example of a method for processing data of an X-ray imaging system.

FIG. 12 is a schematic flow diagram illustrating an example of a method for processing data of an CT imaging system. The schematic flow diagram in FIG. 12 has several features in common with the schematic flow diagram in FIG. 11, and it is hereby referred to FIG. 11 and the associated text for an increased understanding of at least some of the features and/or functions in the flow diagram. In FIG. 12, the illustrated method takes sampled digital detector data, performs filtering according to a filtering setting on the sampled digital detector data, and subsequently resamples the filtered detector data according to a resampling setting. In an example, several steps of resampling and/or filtering may be performed in series.

By way of example, the filtering setting may comprise a bandwidth, an amplitude and/or a set of detector elements. The set of detector elements may be a selection of detector elements. For example, the detector elements may be chosen according to their position in the detector and/or according to a downsampling pattern. The downsampling pattern may e.g., be that a number of neighboring detector elements are binned together, e.g., two or three neighboring detector elements.

Figure 13:
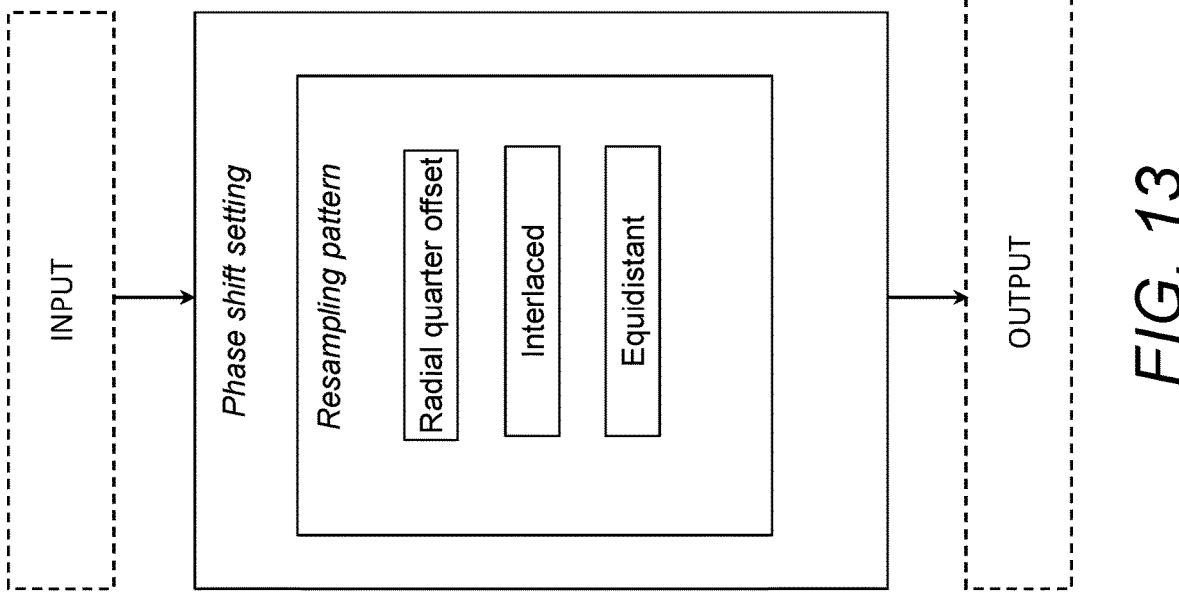
FIG. 13 is a schematic flow diagram illustrating an example of a method for processing data of an X-ray imaging system.

FIG. 13 is a schematic flow diagram illustrating an example of a method for processing data of an CT imaging system. The schematic flow diagram in FIG. 13 has several features in common with the schematic flow diagram in FIGS. 11 and 12, and it is hereby referred to FIG. 11. FIG. 12, and the associated texts for an increased understanding of at least some of the features and/or functions in the flow diagram.

By way of example, the resampling may be performed in a view direction, v. This approach may be performed to form an image of the observed object in the CT imaging system 100, instead of binning different views together with equal weights. This in contrast to performing the resampling in a radial direction r and/or in a longitudinal direction 1 of a detector module.

In a particular example, a filter can be designed and applied in the azimuthal direction prior to resampling in the same direction. This approach may aim to minimize e.g., noise aliasing, signal aliasing and/or azimuthal blur. This scheme may be especially useful when handling data originally collected with flying focal spot and/or view-to-view kV switching. Regarding flying focal spot, the data collected may not be at the desired resampling locations, due to hardware limitations and/or data size considerations. Using phase shifting methods described later, the desired need may be achieved. Regarding view-to-view kV switching, low energy and high energy data may be collected at different azimuthal angles, presenting the need of aligning the data before further processing. This may be fulfilled by using phase shifting methods described later.

In a particular example, the resampling setting may comprise a resampling frequency and/or a phase shift setting.

In a non-limiting example, the resampling frequency may comprise a non-integer resampling frequency. In other words, the steps and/or actions described herein are not limited to integer resampling. The resampling frequency may be reduced by any factor, for example fractional ones. The resampling frequency and phase shift is further discussed in FIG. 15 and associated text.

In another non-limiting example, the phase shift setting may comprise a non-integer phase shift. In other words, the steps and/or actions described herein are not limited to integer phase shifting. Applying a phase shift may be performed in the frequency domain by applying e.g. a linear phase shift. By way of example, after desired adjustments of the amplitude of the frequency components, the inverse Fourier transform may be applied to a half-integer resampling frequency (1.5 or 2.5 etc.) to obtain values at integer sample locations. Furthermore, a linear phase shift followed by a second inverse Fourier transform may be applied to obtain signal samples at half-integer locations. The sought/desired samples may then be selected from the two results.

Phase shift may be performed in the spatial domain by having several different filters. The filters may be designed to accomplish half resample shift. By way of example, a filter without the phase shift properties may be applied to obtain values at any original integer resample location. Furthermore, a filter with the phase shift properties may be applied to obtain resamples at half-integer locations. Such a filter may be a FIR filter, as mentioned herein.

In an exemplifying practical example, a filter may be designed with a bandwidth of a factor of 3 alongside resampling the signal by a factor of 1.5. This example may be beneficial in avoiding aliasing. In another exemplifying practical example, the same resampling factor of 1.5 may be combined with a filter with a bandwidth of 2.5 or 2. This example may be advantageous in allowing higher spatial resolution. This effect may come at a cost in DQE at higher frequencies but may preserve the DQE at low frequencies.

Additionally, the resampling described herein need not be uniform. In other words, the output positions after resampling need not be equally spaced compared to the original input positions. This may be advantageous if the resampled data will subsequently be processed by a fan-to-parallel reconstruction algorithm. When adjusting the data to fit a fan-to-parallel pattern, the samples need to be converted from being equiangular in a fan-beam to being equidistant in a parallel beam geometry. It is worth noting that this approach may be performed during the resampling. This may be desirable as in resulting in a faster processing time, and/or achieving higher signal fidelity.

FIG. 13 is a schematic flow diagram illustrating an example of the resampling according to an embodiment of the invention, and it is hereby referred to FIG. 12 and the associated text for an increased understanding of at least some of the features and/or functions in the flow diagram.

Figure 15:
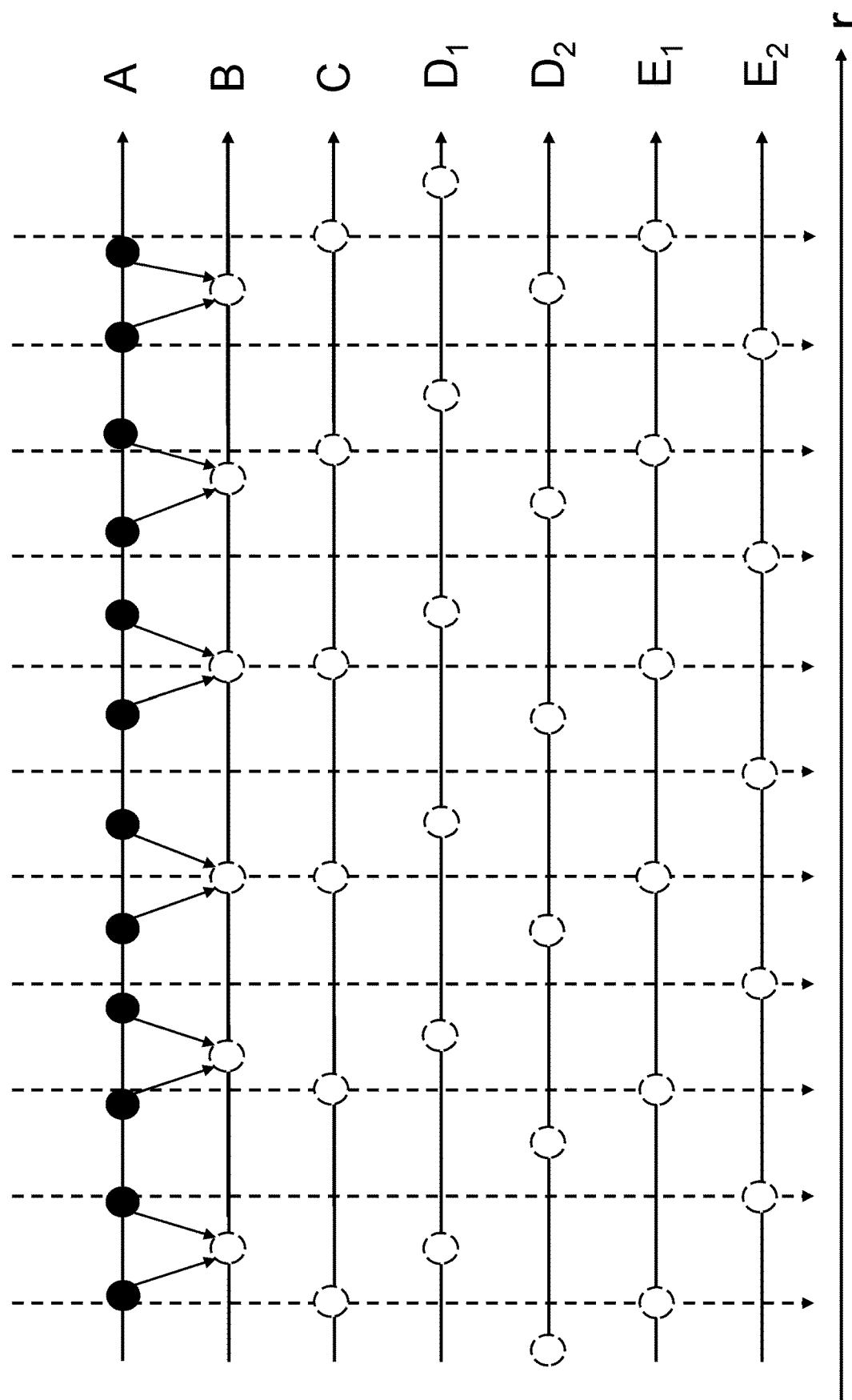
FIG. 15 is a schematic diagram illustrating examples of resampling patterns.

For example, the phase shift setting may be associated with a resampling pattern. The resampling pattern may set how to manage the different data points received after sampling the detector data originally. For example, certain data points may be re-sampled and/or phase shifted to e.g., reduce problems with aliasing and/or noise. Further details on the resampling patterns are shown in FIG. 15 and associated text.

In an exemplifying practical example, the resampling pattern may comprise a radial quarter offset resampling pattern, in a radial direction $r_1$ and/or a longitudinal direction, $l_1$. In other words, the resamples may be offset to one side by one quarter of the resample spacing relative to a perfectly symmetric resampling pattern. This may result in that the conjugate projections lines are completely interleaved after e.g., half of a rotation of the gantry 111. The pattern may be designed to achieve the radial quarter offset digitally and/or virtually. This is advantageous in that it may further reduce aliasing in the resulting images from the X-ray imaging system 100.

In another exemplifying practical example, the resampling pattern may comprise an equidistant resampling pattern, in a radial direction $r_2$ and/or a longitudinal direction, $l_2$.

In yet another exemplifying practical example, the resampling pattern may comprise an interlaced resampling pattern, in a radial direction $r_3$ and/or a longitudinal direction, $l_3$. This may be achieved by selecting the resampling positions such that they shift back and forth between views. The resampling pattern may result in that successive projections form two interlaced radial patterns. The resampling pattern is advantageous in that signal aliasing can be suppressed while not requiring conjugate projections. Therefore, the resampling may be compatible with half-scan CT imaging.

It should be noted that the radial directions $r_1$, $r_2$ and/or $r_3$ may coincide. It should also be noted that the longitudinal directions $l_1$, $l_2$ and/or $l_3$ may as well coincide. Furthermore, whereas resampling is performed in the longitudinal direction $l_1$, $l_2$ and/or $l_3$, the resampling positions may be chosen to obtain the effect of z-flying focal spot. This approach may be advantageous in that a higher spatial resolution is obtained, and/or a reduction in noise level.

Optionally, the interlaced resampling pattern may be formed from at least two successive projections.

Figure 14:
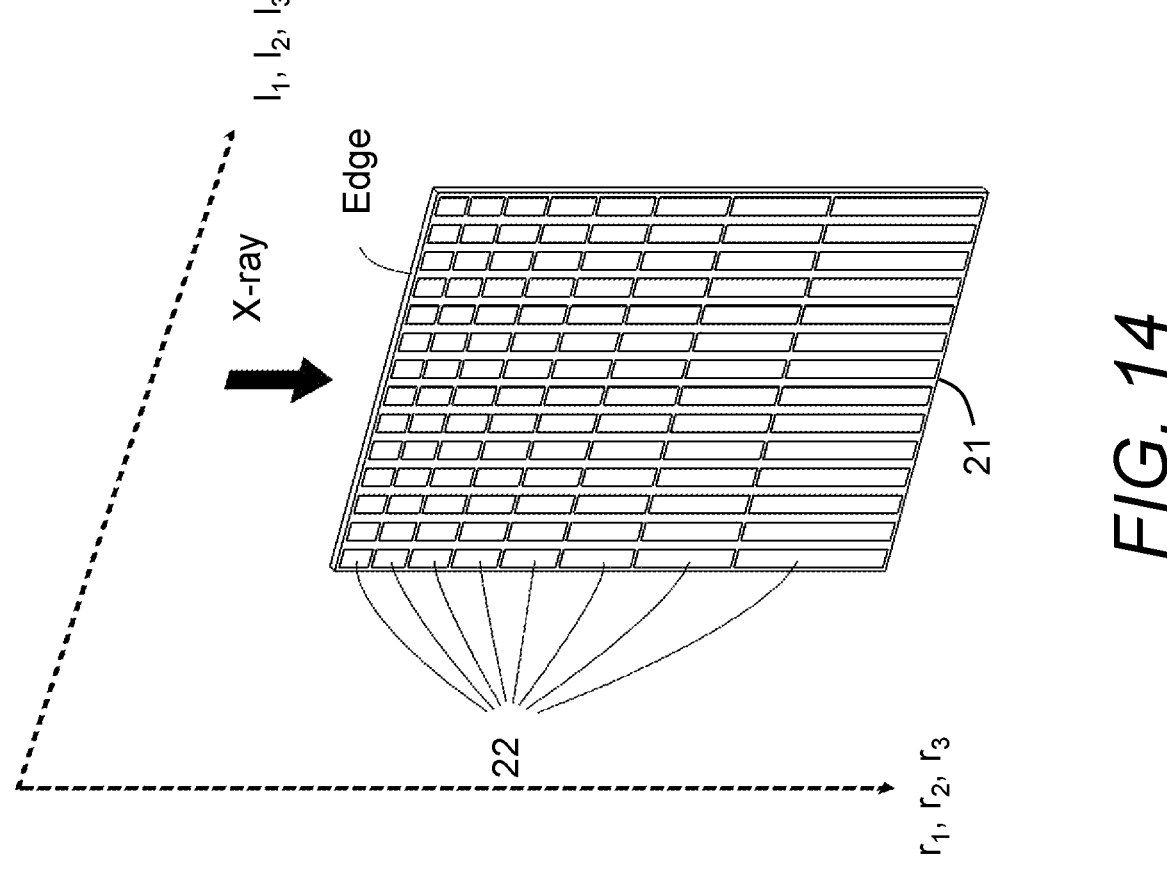
FIG. 14 is a schematic diagram illustrating an example of semiconductor detector sub-module according to an exemplary embodiment.

FIG. 14 is a schematic diagram illustrating an example of semiconductor detector sub-module according to an exemplary embodiment. The semiconductor detector sub-module 21 in FIG. 14 has several features in common with the semiconductor detector sub-module 21 in FIG. 7, and it is hereby referred to FIG. 7 and the associated text for an increased understanding of at least some of the features and/or functions in the detector sub-module 21.

In FIG. 14, coordinate systems $(r_1; l_1)$, $(r_2; l_2)$, and $(r_3; l_3)$ are shown. As mentioned earlier, the resampling may be performed in the radial direction r and/or the longitudinal direction 1 shown in FIG. 14. It should once again be noted that the radial directions $r_1$, $r_2$ and/or $r_3$ may coincide. Again, it should also be noted that the longitudinal directions $l_1$, $l_2$ and/or $l_3$ may as well coincide. The radial direction r may be recognized as the channel or column direction of the detector sub-module 21. Furthermore, the longitudinal direction 1 may be recognized as the row direction of the detector sub-module 21.

FIG. 15 is a schematic diagram illustrating examples (A-E) of sampling and resampling patterns. The axis r represents the radial distance between the sampling positions or the resampling positions, and the dashed vertical lines are equally spaced in radial distance. A illustrates an original equiangular sampling pattern. B illustrates simple binning samples based on sample pattern example A), of neighboring detector channels. C illustrates resampling samples based on resample pattern example B, according to an equidistant resampling pattern. $D_1$-$D_2$ illustrates resampling samples based on resample pattern example B, according to a radial quarter offset resampling pattern. $E_1$-$E_2$ illustrates resampling samples based on resample pattern example B), according to a radial interlaced resampling pattern.

It is worth noting that the samples in example A are positioned closer together for larger fan angles than for smaller fan angles, i.e., away from the center of the axis r.

The samples in example B are still equiangular after the simple binning, but not equally spaced in radial distance. The arrows map the simple binning of the neighboring detector channels.

The samples in example C are both equiangular and equidistant radially, i.e., following a parallel beam geometry.

The samples in examples $D_1$-$D_2$ represents the resampling for direct and conjugate X-rays, respectively.

The samples in examples $E_1$-$E_2$ represents the resampling for two consecutive views. Performing resampling with the resampling pattern shown in $E_1$-$E_2$ may provide the same effect of focal spot deflection, without moving the focal spot of the CT imaging system.

The present disclosure relates to a novel system architecture and corresponding procedures for improved data processing and management for CT imaging systems.

According to a second aspect there is provided a CT imaging system 100 comprising an X-ray source 110 configured to emit X-rays, an X-ray detector 120 configured to generate sampled digital detector data; and a digital processor 140 configured to process the sampled digital detector data. The digital processor 140 is configured to filter the sampled digital detector data according to a filtering setting to generate filtered detector data and resample the filtered detector data according to a resampling setting to generate resampled detector data. The data size of the resampled detector data is smaller than the data size of the filtered detector data. The filtering setting and the resampling setting are decoupled. The CT imaging system is configured to perform the filtering and the following resampling in a decoupled manner, in other words. In other words, the digital processor is configured to perform filtering with a certain filter setting, and the digital processor is configured to perform the resampling on the filtered detector data according to a resampling setting, where the filtering setting and resampling setting is decoupled. Accordingly, a certain filter setting may be used, and resampling may be performed on the filtered data according to a resampling setting that can be adjusted freely in order to generate resampled detector data that can be optimized for a specific purpose, e.g., optimizing resolution/image quality vs speed, or resolution/image quality vs radiation dose. Furthermore, the filter setting and resampling setting may be chosen in accordance with obtaining a desired reduction of the size of the data.

Figure 16:
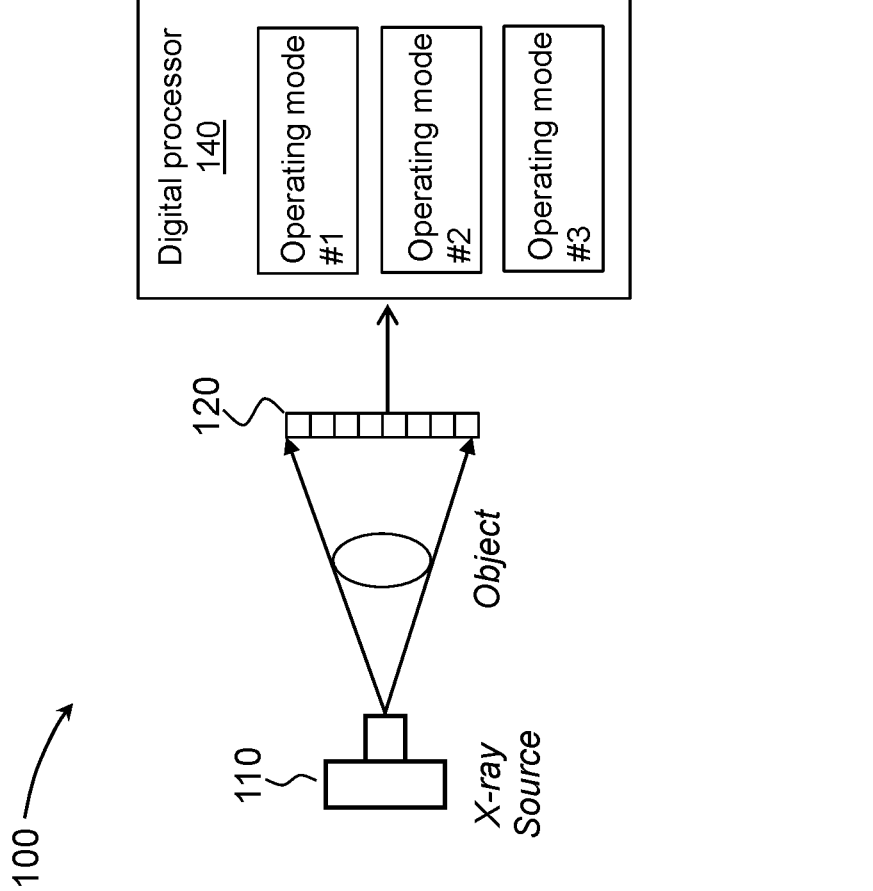
FIG. 16 is a schematic diagram illustrating an example of relevant parts of an X-ray imaging system in a CT configuration.

FIG. 16 is a schematic diagram illustrating an example of relevant parts of an X-ray imaging system in such a CT imaging system.

By way of example, the digital processor may be configured to reduce the data size of the filtered detector data by resampling. The digital processor may be configured to reduce the data size with a reduction factor, and at least one of the filtering setting and resampling setting may be associated with the reduction factor.

In another example, the digital processor is configured to filter and resample the sampled digital detector data to achieve a predetermined image quality. The filtering setting and resampled setting may be set to provide/achieve a certain image quality. The image quality may comprise at least one of spatial resolution, noise level and aliasing level.

In yet another example, the digital processor is configured to resample the generated resampled detector data according to a second resampling setting to generate second resampled detector data. In other words, the digital processor is configured to perform a first resampling according to a first resampling setting, and a second resampling according to a second resampling setting. The first and second resampling settings may be chosen to improve the image quality. The image quality may have deteriorated after the filtering and/or the first resampling stage. The digital processor may be configured to set/chose the resampling setting and the second resampling setting to provide an image of desired image quality. The first resampling may involve a reduction in data size of the filtered detector data given as input. Furthermore, the first resampling may result in a lowered/deteriorated image quality. The second resampling may be set/chosen to at least partially restore the image quality.

Optionally, the digital processor 140 may be configured to operate in one or more operating modes, wherein an operating mode is associated with an image quality, a radiation dose, a DQE metric and/or a data handling scheme.

In a non-limiting example, the resampling setting may comprise a non-integer resampling frequency.

In another non-limiting example, the resampling setting may comprise a non-integer phase-shift setting.

In a practical embodiment, the resampling setting may comprise a phase-shift setting associated with a resampling pattern.

For example, the resampling pattern may comprise a radial quarter offset resampling pattern, in a radial direction $r_1$ and/or a longitudinal direction, $l_1$. The resampling pattern further comprises an equidistant resampling pattern, in a radial direction $r_2$ and/or a longitudinal direction, $l_2$, and an interlaced resampling pattern, in a radial direction $r_3$ and/or a longitudinal direction, $l_3$.

It should be noted that the radial directions $r_1$, $r_2$ and/or $r_3$ may coincide. It should also be noted that the longitudinal directions $l_1$, $l_2$ and/or $l_3$ may as well coincide.

In this example, the CT system includes an X-ray source 110 and an X-ray detector 120 arranged in the beam path of the X-rays in such a way that projection images of the subject or object can be acquired in different viewing angles. This is most commonly achieved by mounting the X-ray source 110 and the X-ray detector 120 on a support, e.g., a rotating member of a gantry, that is able to rotate around the subject or object.

The proposed technology enables an improved and versatile way to perform filtering and resampling of detector data, e.g., to enable efficient handling of large amounts of detector data and/or to mitigate potential bottleneck effects in traditional CT imaging systems.

In this way, the proposed technology makes it possible to more optimally exploit the superior imaging potential of modern X-ray detectors such as high-resolution, photon counting, energy-discriminating and/or multi-segment detectors.

Thus, the proposed technology may effectively handle tradeoffs between image quality related to e.g., resolution and/or aliasing, radiation dose, data size, data fidelity and practical constraints related to computational resources, electrical power, cooling, space and/or data transfer bandwidth.

By way of example, the CT imaging system 100 may comprise a gantry 111 including a rotating member on a rotating side 102 and a stationary member on a stationary side 104. The rotating member and the stationary member are communicatively coupled via a data communication system 160, wherein the rotating member comprises the X-ray source 110, the X-ray detector 120 and the digital processor 140. Processed detector data may be transferred from the rotating (moving) side of the gantry to the stationary side of the gantry.

The data communication system 160 may be a slip ring typically used in CT imaging systems with a rotating member of a gantry. By "slip ring" it is here meant an electro-mechanical device that allows the transmission of power and electrical signals, e.g., power and data transfer between a rotating structure and a stationary structure.

In a particular example, the digital processor 140 may comprise a first digital processor 140-1 arranged on the rotating member and a second digital processor 140-2 arranged on the stationary member. The first and/or second digital processor is configured to perform at least part of the filtering and/or the resampling.

Preferably, the CT imaging system 100 may comprise a data storage unit 150 configured to store at least part of the sampled digital detector data, the filtered detector data and/or the resampled detector data. The CT imaging system 100 may have a first data storage unit 150-1 arranged on a rotating side 102 of a CT imaging system, and a second data storage unit 150-2 arranged on a stationary side 104 of a CT imaging system. An example of this is illustrated in FIG. 17.

As mentioned, at least some of the steps, functions, procedures, and/or blocks described herein may be implemented in software such as a computer program for execution by suitable processing circuitry such as one or more processors or processing units.

Figure 18:
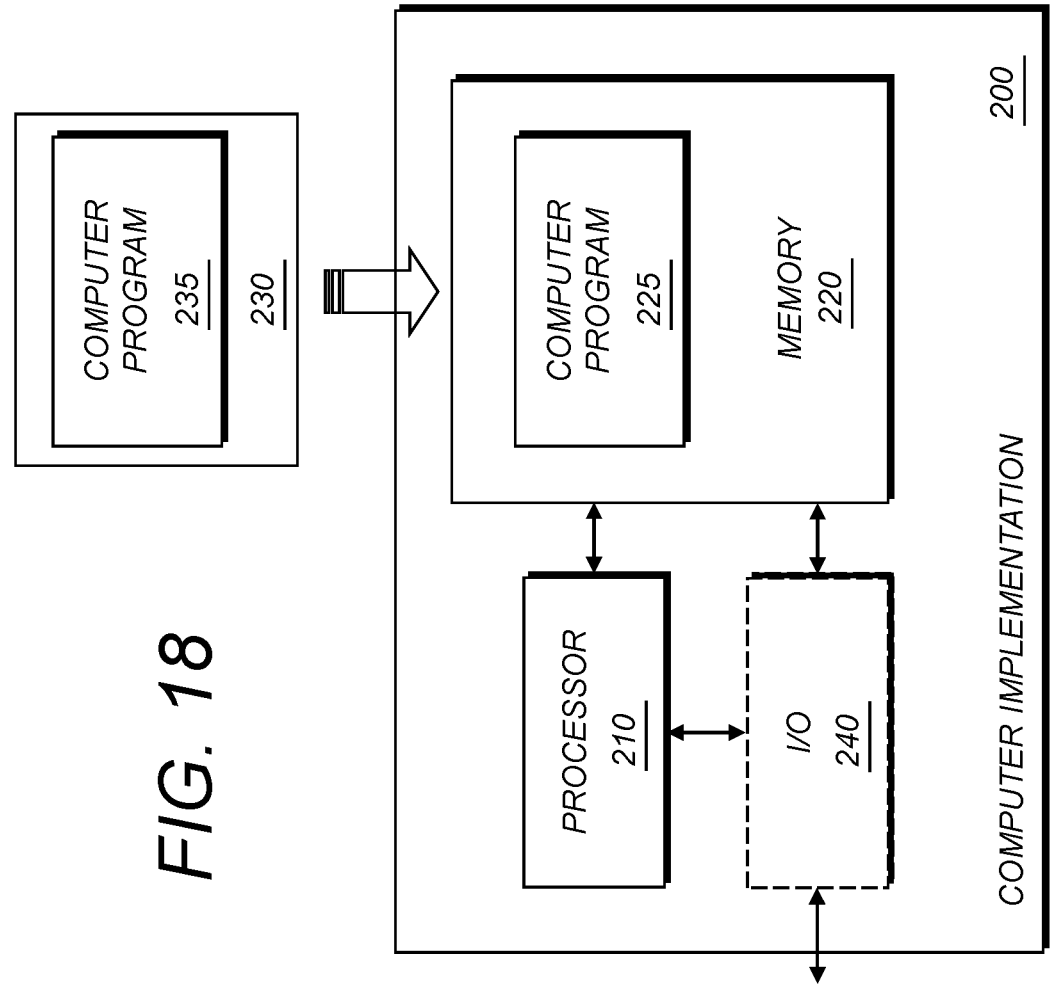
FIG. 18 is a schematic diagram illustrating an example of a computer implementation according to an embodiment.

FIG. 18 is a schematic diagram illustrating an example of a computer implementation according to an embodiment.

In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

In a particular example, the memory 220 comprises a set of instructions executable by the processor, whereby the processor is operative to perform the steps and/or actions described herein.

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possible to realize the modules predominantly by hardware modules, or alternatively by hardware. The extent of software versus hardware is purely implementation selection.

Embodiments of the present disclosure shown in the drawings and described above are example embodiments only and are not intended to limit the scope of the appended claims, including any equivalents as included within the scope of the claims. It will be understood by those skilled in the art that various modifications, combinations, and changes may be made to the embodiments without departing from the present scope as defined by the appended claims. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

It is further noted that the inventive concepts relate to all possible combinations of features unless explicitly stated otherwise. In particular, different part solutions in the different embodiments can be combined in other configurations, where technically possible.

The invention claimed is:

1. A method for processing computed tomography (CT) data in a CT imaging system, the CT imaging system comprising:

an X-ray source configured to emit X-rays;

an X-ray detector configured to generate sampled digital detector data;

a digital processor configured to process the sampled digital detector data;

the method comprising:

filtering, in the digital processor, the sampled digital detector data to generate filtered detector data, wherein the filtering is performed in the spatial domain;

resampling, in the digital processor, the filtered detector data to generate resampled detector data, wherein the resampling comprises a reduction in data size of the filtered detector data and is performed using an interlaced resampling pattern;

and wherein the filtering setting and resampling setting are decoupled and independently selected based on an operating mode that balances image quality, radiation dose, and data handling efficiency.

2. The method according to claim 1, wherein the reduction in data size reduces the data size with a reduction factor, and wherein at least one of the filtering setting and resampling setting is associated with the reduction factor.

3. The method according to claim 1, wherein the filtering setting and resampled setting are set to achieve a predetermined image quality.

4. The method according to claim 3, wherein the image quality comprises at least one of spatial resolution, noise level and aliasing level.

5. The method according to claim 1, wherein the filtering is performed in at least one of the spatial and frequency domain.

6. The method according to claim 1, wherein the resampling is performed in at least one of the spatial and frequency domain.

7. The method according to claim 1, wherein the resampling comprises a first resampling according to a first resampling setting and a second resampling according to a second resampling setting.

8. The method according to claim 1, wherein the filtering setting comprises at least one of a bandwidth, an amplitude and a set of detector elements.

9. The method according to claim 1, wherein the resampling setting comprises at least one of a resampling frequency and a phase shift setting.

10. The method according to claim 9, wherein the resampling frequency comprises at least one of a non-integer resampling frequency and a non-integer phase shift.

11. The method according to claim 9, wherein the phase shift setting is associated with a resampling pattern.

12. The method according to claim 1, wherein the CT imaging system comprises a gantry including a rotating member of the gantry on a rotating side of the gantry and a stationary member of the gantry on a stationary side of the gantry, the rotating member and the stationary member being communicatively coupled via a data communication system, wherein the rotating member includes the X-ray source, the X-ray detector and the digital processor.

13. A CT imaging system comprising:

an X-ray source configured to emit X-rays;

an X-ray detector configured to generate sampled digital detector data; and a digital processor configured to process the sampled digital detector data, wherein the digital processor is configured to:

filter the sampled digital detector data according to a filtering setting to generate filtered detector data, wherein the filtering is performed in the spatial domain; and resample the filtered detector data according to a resampling setting to generate resampled detector data and is performed using an interlaced resampling pattern; and wherein the filtering setting and the resampling setting are decoupled and independently selected based on an operating mode that balances image quality, radiation dose, and data handling efficiency.

14. The CT imaging system according to claim 13, further comprising a gantry including a rotating member of the gantry on a rotating side of the gantry and a stationary member of the gantry on a stationary side of the gantry, the rotating member and the stationary member being communicatively coupled via a data communication system, wherein the rotating member includes the X-ray source, the X-ray detector and the digital processor.

15. The CT imaging system according to claim 14, wherein the digital processor comprises a first digital processor arranged on the rotating member and a second digital processor arranged on the stationary member, wherein at least one of the first and second digital processor is configured to perform at least part of the filtering and/or the resampling.

16. The CT imaging system according to claim 13, wherein the CT imaging system comprises a data storage unit configured to store at least part of the sampled digital detector data, the filtered detector data and/or the resampled detector data.

17. The CT imaging system according to claim 13, wherein the digital processor is configured to operate in one or more operating modes, wherein an operating mode is associated with at least one of an image quality, a radiation dose, a DQE metric and a data handling scheme.

18. The CT imaging system according to claim 13, wherein the resampling setting comprises at least one of a non-integer resampling frequency and a non-integer phase-shift setting.

19. The CT imaging system according to claim 13, wherein the digital processor is configured to resample the generated resampled detector data according to a second resampling setting to generate second resampled detector data.

20. The CT imaging system according to claim 13, wherein the resampling setting comprises a phase-shift setting associated with a resampling pattern.

21. The CT imaging system according to claim 20, wherein the resampling pattern comprises at least one of:

a radial quarter offset resampling pattern, in at least one of a radial direction $r_1$ and a longitudinal direction, $l_1$;

an equidistant resampling pattern, in at least one of a radial direction $r_2$ and a longitudinal direction, $l_2$; and an interlaced resampling pattern, in at least one of a radial direction $r_3$ and a longitudinal direction, $l_3$.

* * * * *